US009486140B2

(12) United States Patent
Tang et al.

(10) Patent No.: US 9,486,140 B2
(45) Date of Patent: Nov. 8, 2016

(54) COHERENCE GATED DOPPLER MOTION SENSOR AND MEDICAL APPLICATIONS

(71) Applicants: University of Maryland, Baltimore, Baltimore, MD (US); University of Maryland, College Park, College Park, MD (US); St. Jude Medical, Westford, MA (US); The United States of America as represented by the Department of Veterans Affairs, Washington, DC (US)

(72) Inventors: Cha-Min Tang, Radnor, PA (US); Chia-Pin Liang, College Park, MD (US); Yu Chen, Greenbelt, MD (US); Ashraf Fouad, Baltimore, MD (US); Joseph Schmitt, Andover, MA (US); Nicholas Woolsey, Hudson, MA (US)

(73) Assignees: University of Maryland, Baltimore, Baltimore, MD (US); The United States of America as represented by the Department of Veterans Affairs, Washington, DC (US); St. Jude Medical, Westford, MA (US); University of Maryland, College Park, College Park, MD (US)

( * ) Notice: Subject to any disclaimer, the term of this patent is extended or adjusted under 35 U.S.C. 154(b) by 156 days.

(21) Appl. No.: 13/962,450

(22) Filed: Aug. 8, 2013

(65) Prior Publication Data

US 2014/0043618 A1 Feb. 13, 2014

Related U.S. Application Data

(60) Provisional application No. 61/680,788, filed on Aug. 8, 2012.

(51) Int. Cl.
*G01B 11/02* (2006.01)
*A61B 5/00* (2006.01)
(Continued)

(52) U.S. Cl.
CPC .......... *A61B 5/0059* (2013.01); *A61B 5/0066* (2013.01); *A61B 5/0084* (2013.01);
(Continued)

(58) Field of Classification Search
CPC .. A61B 5/0059; A61B 5/0084; A61B 5/489; A61B 5/0066; A61B 5/026; A61B 5/0261; A61B 5/7415; A61B 5/7405; A61B 5/742; A61B 5/0088; A61C 19/04
USPC ......................................... 356/498, 479, 497
See application file for complete search history.

(56) References Cited

U.S. PATENT DOCUMENTS

| 2004/0176688 | A1* | 9/2004 | Haldeman ..................... 600/443 |
| 2008/0018907 | A1* | 1/2008 | Beaulieu ............ G01B 9/02044 356/482 |
| 2013/0169759 | A1* | 7/2013 | Godavarty ........... A61B 5/0073 348/47 |

OTHER PUBLICATIONS

Ding et al, Real-time phase-resolved optical coherence tomography and optical Doppler tomograph, Mar. 11, 2002 | vol. 10, No. 5 | Optics Express 236.*

(Continued)

*Primary Examiner* — Tarifur Chowdhury
*Assistant Examiner* — Jonathon Cook
(74) *Attorney, Agent, or Firm* — Eugene J. Molinelli; Buesse Wolter Sanks & Maire

(57) ABSTRACT

A motion sensor applicable to medical procedures includes a source of light with a wavelength bandwidth and an optical detector. A first optical coupler terminates in a first probe tip and couples the light into the first probe tip. A second optical coupler terminates in a second probe tip and directs onto the detector scattered light returning through the second probe tip. A presentation device outputs a signal that indicates motion in a target volume of a sample in a vicinity of the probe tips based on a Doppler shift of the scattered light. The volume depends on coherence distance determined by the bandwidth. In variations, the first and second tips are the same tip, a multimode fiber is included, the bandwidth is between 0.1% and 5% of a center wavelength, or the presentation device is a speaker, or some combination.

24 Claims, 18 Drawing Sheets

(51) Int. Cl.
    A61B 5/026    (2006.01)
    A61C 19/04   (2006.01)
(52) U.S. Cl.
    CPC ............ *A61B5/0261* (2013.01); *A61B 5/489*
        (2013.01); *A61B 5/7415* (2013.01); *A61B*
        *5/0088* (2013.01); *A61C 19/04* (2013.01)

(56) References Cited

OTHER PUBLICATIONS

Adeel Ahmad et al., "Sonification of optical coherence tomography data and images", "Optics Express", 2010, pp. 9934-9944, vol. 18, No. 10, Publisher: Optical Society of America, Published in: http://www.opticsinfobase.org/oe/abstract.cfm?uri=oe-18-10-9934.

Devin K. Binder et al., "Hemorrhagic Complications of Microelectrode-Guided Deep Brain Stimulation", "Stereotactic and Functional Neurosurgery", 2003, pp. 28-31, vol. 80, Publisher: Karger AG, Published in: New York, NY.

Zhongpin Chen et al., "Noninvasive imaging of in vivo blood flow velocity using optical Doppler tomography", "Optics Letters", 1997, pp. 1119-1121, vol. 22, No. 14, Publisher: Optical Society of America, Published in: http://www.opticsinfobase.org/ol/issue.cfm?volume=22&issue=14.

Zhongpin Chen et al., "Optical Doppler Tomography", "IEEE Journal of Selected Topics in Quantum Electronics", 1999, pp. 1134-1142, vol. 5, No. 4, Publisher: IEEE, Published in: http://ieeexplore.ieee.org/xpl/tocresult.jsp?isnumber=17287&punumber=2944.

Hee Chul Eun, "Evaluation of Skin Blood Flow by Laser Doppler Flowmetry", "Clinics in Dermatology", 1995, pp. 337-347, vol. 13, Publisher: Elsevier Science Inc., Published in: New York, NY.

Ingemar Fredriksson et al., "Laser Doppler Flowmetry—a Theoretical Framework", 2007, pp. 1-22, Publisher: Department of Biomedical Engineering, Linkoping University, Published in: www.imt.liu.se/bit/ldf/ldfmain.html.

Julius M. Gardin et al., "Evaluation of blood flow velocity in the ascending aorta and main pulmonary artery of normal subjects by Doppler . . . ", "American Heart Journal", 1984, pp. 310-319, vol. 107, No. 2, Publisher: Elsevier, Published in: New York, NY.

Bertil Gazelius et al., "Restored vitality in luxated teeth assessed by laser Doppler flowmeter", "Endodontics and Dental Traumatology", 1988, pp. 265-268, vol. 4.

Thomas Grau et al., "Efficacy of Ultrasound Imaging in Obstetric Epidural Anesthesia", "Journal of Clinical Anesthesia", 2002, pp. 169-175, vol. 14, Publisher: Elsevier Science Inc., Published in: New York, NY.

Robert S. Jones et al., "Near-infrared transillumination at 1310-nm for the imaging of early dental decay", "Optics Express", 2003, pp. 2259-2265, vol. 11, No. 18, Publisher: Optical Society of America, Published in: http://www.opticsinfobase.org/oe/issue.cfm?volume=11&issue=18.

Dimitrios Karakitsos et al., "Real-time ultrasound-guided catheterisation of the internal jugular vein: a prospective comparison with . . . ", "Critical Care", 2006, pp. 18, vol. 10, No. 6, Publisher: BioMed Central Ltd., Published in: http://ccforum.com/content/10/6/R162.

Kanittha Kijsamanmith et al., "Pulpal blood flow recorded from human premolar teeth with a laser Doppler flow meter using either red or infrared light", "Archives of Oral Biology", 2011, pp. 629-633, vol. 56, Publisher: Elsevier, Published in: www.sciencedirect.com.

Ranier Leitgeb et al., "Performance of fourier domain vs. time domain optical coherence tomography", "Optics Express", 2003, pp. 889-894, vol. 11, No. 8, Publisher: Optical Society of America, Published in: http://www.opticsinfobase.org/oe/issue.cfm?volume=11&issue=8.

Darren Morofke et al., "Wide dynamic range detection of bidirectional flow in Doppler optical coherence tomography using a two-dimensional . . . ", "Optics Letters", 2007, pp. 253-255, vol. 32, No. 3, Publisher: Optical Society of America, Published in: http://www.opticsinfobase.org/ol/issue.cfm?volume=32&issue=3.

L. Olgart et al., "Laser Doppler flowmetry in assessing vitality in luxated permanent teeth", "International Endodontic Journal", 1988, pp. 300-306, vol. 21, No. 5, Publisher: Wiley Online Library, Published in: http://onlinelibrary.wiley.com/doi/10.1111/j.1365-2591.1988.tb01139.x/pdf.

Kerstin Petersson et al., "Evaluation of the ability of thermal and electrical tests to register pulp vitality", "Endodontic and Dental Traumatology", 1999, pp. 127-131, vol. 115, Publisher: Munksgaard, Published in: Denmark.

Anna L. Petoukhova et al., "Path-length distribution and path-length-resolved Doppler measurements of multiply scattered photons by . . . ", "Optics Letters", 2001, pp. 1492-1494, vol. 26, No. 19, Publisher: Optical Society of America, Published in: http://www.opticsinfobase.org/ol/issue.cfm?volume=26&issue=19.

Stefan K. Piechnik et al., "Modelling vascular reactivity to investigate the basis of the relationship between cerebral blood volume and flow . . . ", "NeuroImage", 2008, pp. 107-118, vol. 39, Publisher: Elsevier Inc., Published in: www.elsevier.com/locate/ynimg.

Maria Helena Pozzobon et al., "Assessment of pulp blood flow in primary and permanent teeth using pulse oximetry", "Dental Traumatology", 2011, pp. 184-188, vol. 27, No. 3, Publisher: John Wiley & Sons, Published in: http://onlinelibrary.wiley.com/doi/10.1111/edt.2011.27.issue-3/issuetoc.

Vinayakrishnan Rajan et al., "Review of methodological developments in laser Doppler flowmetry", "Lasers in Medical Science", 2009, pp. 269-283, vol. 24, No. 2, Publisher: Springer, Published in: http://link.springer.com/article/10.1007/s10103-007-0524-0.

Joseph M. Schmitt et al., "Optical Determination of Dental Pulp Vitality", "IEEE Transactions on Biomedical Engineering", 1991, pp. 346-352, vol. 38, No. 4, Publisher: IEEE, Published in: http://ieeexplore.ieee.org/xpl/tocresult.jsp?isnumber=3655&punumber=10.

S. Soo-Ampon et al., "The sources of laser Doppler blood-flow signals recorded from human teeth", "Archives of Oral Biology", 2003, pp. 353-360, vol. 48, No. 5, Publisher: Elsevier, Published in: http://www.aobjournal.com/.

Babu Varghese et al., "Path-length-resolved measurements of multiple scattered photons in static and dynamic turbid media using . . . ", "Journal of Biomedical Optics", 2007, pp. 0240201-0240207, vol. 12, No. 2, Publisher: Society of Photo-Optical Instrumentation Engineers, Published in: http://biomedicaloptics.spiedigitallibrary.org/.

Babu Varghese et al., "In Vivo Optical Path Lengths and Path Length Resolved Doppler Shifts of Multiply Scattered Light", "Lasers in Surgery and Medicine", 2010, pp. 852-860, vol. 42, No. 6, Publisher: Wiley-Liss, Inc., Published in: http://onlinelibrary.wiley.com/doi/10.1002/lsm.v42:9/issuetoc.

Karin Wardell et al., "Intracerebral Microvascular Measurements during Deep Brain Stimulation Implantation using Laser Doppler Perfusion . . . ", "Stereotactic and Functional Neurosurgery", 2007, pp. 279-286, vol. 85, No. 6, Publisher: C. Karger AG, Published in: http://www.karger.com/Journal/Issue/233719.

Rebeca Weisleder et al., "The Validity of Pulp Testing: A Clinical Study", "Journal of the American Dental Association", 2009, pp. 1013-1017, vol. 140, No. 8, Publisher: American Dental Association, Published in: http://jada.ada.org/content/140/8/1013.

Volker Westphal et al., "Real-time, high velocity-resolution color Doppler optical coherence tomography", "Optics Letters", 2002, pp. 34-36, vol. 27, No. 1, Publisher: Optical Society of America, Published in: http://www.opticsinfobase.org/ol/issue.cfm?volume=27&issue=1.

Victor X. D. Yang et al., "High speed, wide velocity dynamic range Doppler optical coherence tomography (Part I): System design . . . ", "Optics Express", 2003, pp. 794-809, vol. 11, No. 7, Publisher: Optical Society of America, Published in: http://www.opticsinfobase.org/oe/issue.cfm?volume=11&issue=7.

* cited by examiner

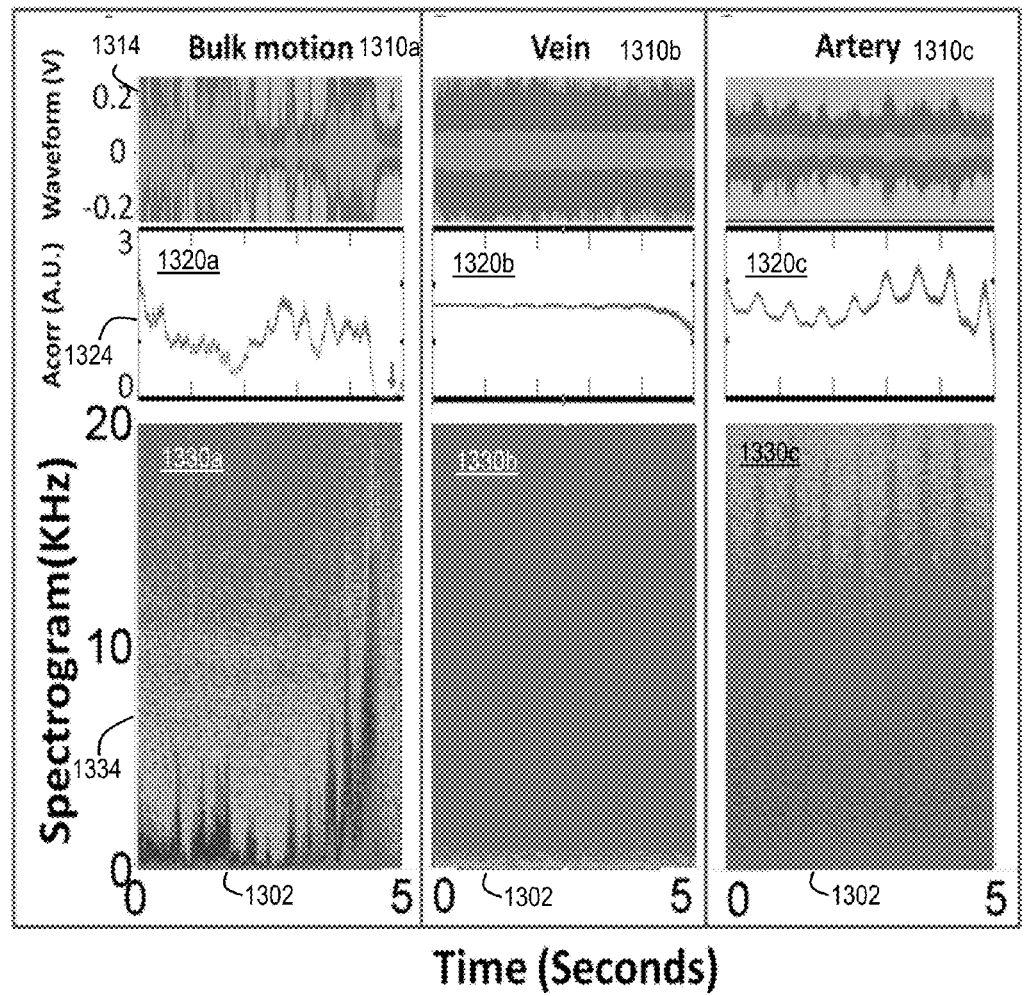

COHERENCE GATED DOPPLER MOTION SENSOR AND MEDICAL APPLICATIONS

CROSS-REFERENCE TO RELATED APPLICATIONS

This application claims benefit of Provisional Appln. 61/680,788, filed Aug. 8, 2012, the entire contents of which are hereby incorporated by reference as if fully set forth herein, under 35 U.S.C. §119(e).

BACKGROUND OF THE INVENTION

Motion sensors have a wide range of applications and are implemented using a wide range of techniques exploiting a wide range of physical principles. Medical applications for motion sensors include diagnosis and treatment of a subject based on the presence, function or location of blood vessels that carry moving blood cells and other constituents. Sometimes the tissue, such as bone, is difficult to penetrate for obtaining the motion measurement. Only a few motion sensors are suitable for such varied medical applications.

One technique that has been used in medical applications is laser Doppler flowmetry (LDF). As stated in Marc F. Swiontkowski, "Laser Doppler Flowmetry—Development and Clinical Application," *Iowa Orthopaedic Journal*, v11, pp 119-126 (1991), "Laser Doppler Flowmetry (LDF) is an accurate and reliable method for assessing microcirculatory function. Through a series of in vitro and in vivo experiments, LDF output has been shown to be reproducible and to correlate with bone blood flow as estimated by other methods. The utility of the method in assessing meniscal, tendonous, and ligamentous perfusion has also been demonstrated. LDF has proven potential in clinical research in osteonecrosis, osteomyelitis, fracture healing, and other areas." LDF has also been applied to neurosurgery, dermatology and dentistry. However, these devices suffer from low signal to noise ratio and low spatial resolution compared to blood vessels of interest during many diagnosis and treatment procedures.

Another technique used in medical applications is Doppler optical coherence tomography (DOCT). Optical coherence tomography (OCT) is an optical signal acquisition and processing method. It captures micrometer-resolution, three-dimensional images from within optical scattering media (e.g., biological tissue). Depending on the properties of the light source (superluminescent diodes, ultrashort pulsed lasers and supercontinuum lasers have been employed), optical coherence tomography has achieved sub-micrometer resolution (with very wide-spectrum sources emitting over a range of wavelengths about 100 nanometers wide, 1 nanometer, nm, $=10^{-9}$ meters). Commercially available optical coherence tomography systems are employed in diverse applications, including diagnostic medicine, notably in ophthalmology where it can be used to obtain detailed images from within the retina. Recently it has also begun to be used in interventional cardiology to help diagnose coronary artery disease. Determining the Doppler shift in the returned signal due to motion of the optical scatterers in the sample, turns the OCT into a 3D imaging DOCT motion sensor. However, these devices are expensive, complicated, unwieldy and difficult to use when diagnosing or treating patients.

SUMMARY OF THE INVENTION

Techniques are provided for simple, inexpensive, reliable, easily-used motion sensors with sufficiently high resolution to detect, locate and distinguish blood vessels during medical procedures as well as fluid carrying vessels in other applications.

In a first set of embodiments, an apparatus includes an optical source of light comprising a band of wavelengths and an optical detector. The apparatus also includes a first optical coupler configured to direct light from the optical source through an emission optical path that terminates at a distal end in a single probe tip, and a second optical coupler configured to direct onto the optical detector scattered light returning from the single probe tip through a return optical path. The apparatus further includes a presentation device configured to output a signal that indicates motion in a target volume of a sample in a vicinity of the single probe tip based on a Doppler shift between the light from the light source and the scattered light received at the detector through the single probe. The target volume is based, at least in part, on a coherence distance determined by a bandwidth of the band of wavelengths of the light from the optical source. In some embodiments of the first set, the first optical coupler and second optical coupler include a single optical fiber connected to the single probe tip and the single optical fiber is a multimode optical fiber.

In a second set of embodiments, an apparatus includes an optical source of light comprising a band of wavelengths and an optical detector. The apparatus also includes a first optical coupler configured to direct light from the optical source through an emission optical path that terminates at a distal end in a first probe tip, and a second optical coupler configured to direct onto the optical detector, through a return optical path that terminates at a distal end in a second probe tip, scattered light that enters the second probe tip from outside the second probe tip. The apparatus also includes a presentation device configured to output a signal that indicates motion in a target volume of a sample in a vicinity of the first probe tip and second probe tip based on a Doppler shift between the light from the light source emitted through the first probe tip and the scattered light received at the detector through the second probe tip. The target volume is based, at least in part, on a coherence distance determined by a bandwidth of the band of wavelengths of the light from the optical source and the wavelength bandwidth is greater than about 0.1% of a center wavelength of the band of wavelengths. In some embodiments of the second set, the second probe tip is the first probe tip. In some embodiments of the second set, at least one of the first optical coupler and the second optical coupler includes a multimode optical fiber.

In a third set of embodiments, an apparatus includes an optical source of light comprising a band of wavelengths and an optical detector. The apparatus also includes a first optical coupler configured to direct light from the optical source through an emission optical path that terminates at a distal end in a first probe tip. The apparatus also includes a second optical coupler configured to direct, onto the optical detector through a return optical path that terminates at a distal end in a second probe tip, scattered light that enters the second probe tip from outside the second probe tip. The apparatus further includes a speaker configured to output a signal that indicates motion in a target volume of a sample in a vicinity of the first probe tip and second probe tip based on interference at the detector. The target volume is based, at lest in part, on a coherence distance determined by a bandwidth of the band of wavelengths of the light from the optical source. In some embodiments of the third set, the second probe tip is the first probe tip. In some embodiments of the third set, at least one of the emission path and the return path includes a multimode optical fiber. In some embodiments of the third set, the acoustic speaker is an analog acoustic speaker and the detector outputs an analog electronic signal, and the speaker is driven by the analog electronic signal from the detector without an intervening analog to digital converter.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 13A through FIG. 13C are graphs that illustrate results of the application of FIG. 12, according to an embodiment;

DETAILED DESCRIPTION

A method and apparatus are described for a coherence gated Doppler motion sensor. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. In the following, various publications are cited, of which the entire contents of each is hereby incorporated by reference as if fully set forth herein, except for terminology that is inconsistent with the terminology used herein.

Figure 1A:
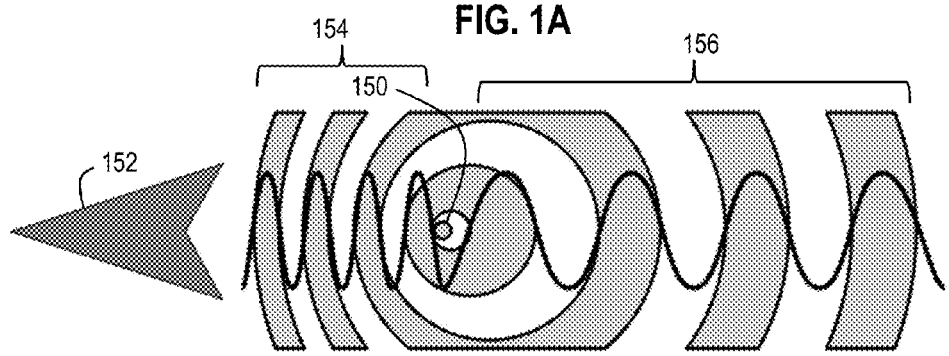
FIG. 1A through FIG. 1C are block diagrams that illustrate an example method to produce an interference signal at a detector, which indicates motion in a target volume.
Figure 1B:
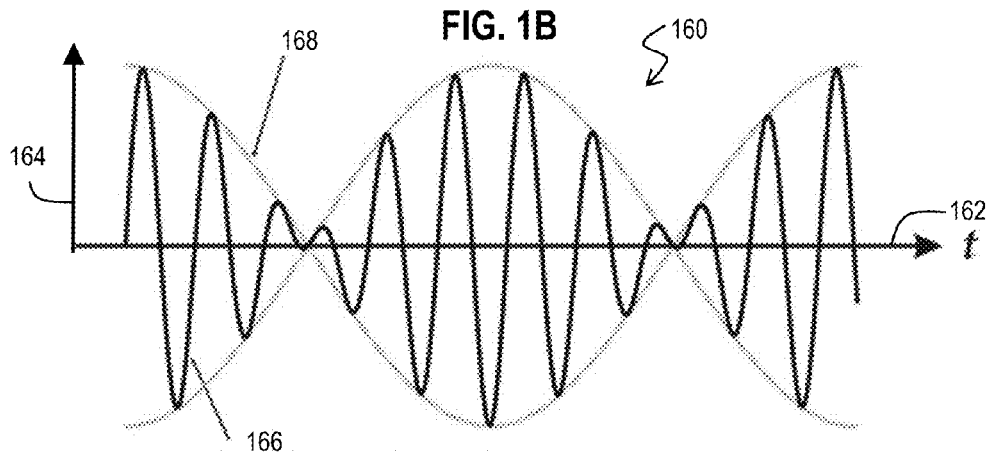
Figure 1C:
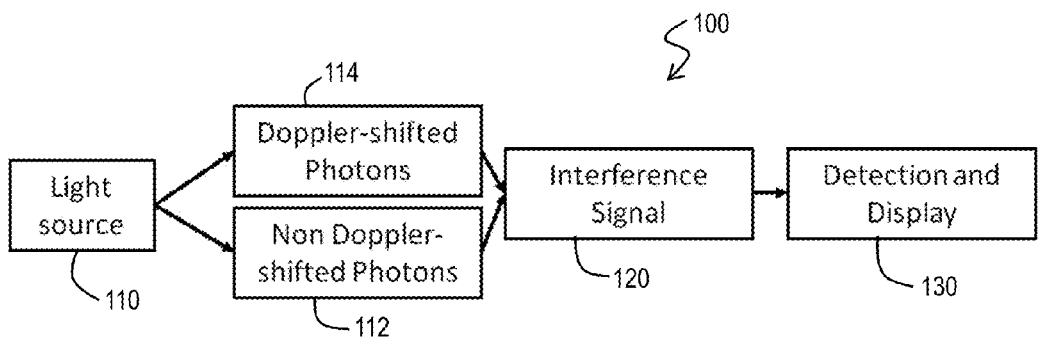

Some embodiments of the invention are described below in the context of a few variations applied in medical examples, including teeth, muscle and brain tissue. However, the invention is not limited to these contexts. In other embodiments the motion sensor comprises a different arrangement of components, using different variations and combinations of the example components given here, and are used in other medical and non-medical applications, including bone, tumor, ocular, pain management, cardiology, catheterization, anesthesia, intravascular procedures, spine procedures and gastrointestinal tissues, in human and animals, in flow cytometry and microfluidics devices, and in machinery and robotics, among others FIG. 1A through FIG. 1C are block diagrams that illustrate an example method to produce an interference signal at a detector, which indicates motion in a target volume. FIG. 1A is a block diagram that illustrates a Doppler shift in frequency and wavelength. A source 150, such as an emitter or scatterer of a wave, such as an electromagnetic wave, including light, is moving in direction 152 relative to an observer. The waves 154 propagating in the direction of movement have an increased frequency and reduced wavelength compared to that emitted or scattered from a stationary source. Similarly, the waves 156 propagating in the direction opposite to the movement have a decreased frequency and increased wavelength compared to that emitted or scattered from a stationary source. This shift in frequency and wavelength is the called a Doppler shift and is proportional to the speed v of the source 150 relative to the observer. For light waves traveling at the speed of light in the medium, given by cN where c is the speed of light in a vacuum and N is the index of refraction of the medium, the Doppler shift $\Delta\lambda$, in original wavelength $\lambda_0$ is given by Equation 1a and frequency shift by Equation 1b for an approaching source 150.

$$\Delta\lambda = -(v/cN)\lambda_0 \tag{1a}$$

$$\Delta f = (v/cN)f_0 \tag{1b}$$

The optical wavelengths are very small, occurring in a range of hundreds of nanometers (nm, 1 nm=$10^{-9}$ meters) and the corresponding frequencies are high on the order of hundreds of terahertz (THz, 1 THz=$10^{12}$ Hertz).

For many applications, such as medical applications with blood flow on the order of a meter per second, the speed v is a tiny fraction of the speed of light in the medium and so the Doppler shift is exceedingly small, on the order of $10^{-8}$ of the wavelength λ or frequency f. Such a change is difficult to measure directly. However, if the Doppler shifted wave interacts with a non-Doppler shifted wave, the interference pattern produces a signal related to the difference between the two waves that is much easier to measure. For example, a speed on the order of 1 meter per second (m/s) for a wavelength of about 1000 nm (f of about 300 THz) has a frequency shift of about 1 MegaHertz (MHz, 1 MHz=$10^6$ Hertz, 1 Hertz, Hz, =1 cycle per second). FIG. 1B is a graph 160 that illustrates an example interference signal between two different waves. The horizontal axis 162 is time in arbitrary units, and the vertical axis 164 is amplitude in arbitrary units. The interference signal is given by trace 166, which is enclosed by an envelope 168 of much lower frequency. Even for interfering optical waves with a frequency shift of one millionth of the optical frequencies, the interference signal envelope 168 has frequency on the order of MegaHertz. For flows of about a millimeter per second, the frequency is on the order of tens of kilohertz (kHz, 1 kHZ=$10^3$ Hertz).

FIG. 1C is a block diagram that illustrates an example motion sensor system 100 based on optical measurements, as employed by many current motion sensor systems. A light source block 110 emits light of which one portion interacts with moving scatterers in block 114 and is Doppler shifted, and another portion is not Doppler shifted in block 112, either because of interaction with stationary scatterers, or because this portion propagates in a reference path free from any scatterers, or some combination. The two paths are brought together to create an interference signal in block 120, which is detected and displayed in block 130. How the different blocks are implemented varies widely in different devices. Two types of existing motion sensor devices are described next: a laser Doppler flowmetry (LDE) device; and a Doppler optical coherence tomography (DOCT) device.

Figure 2A:
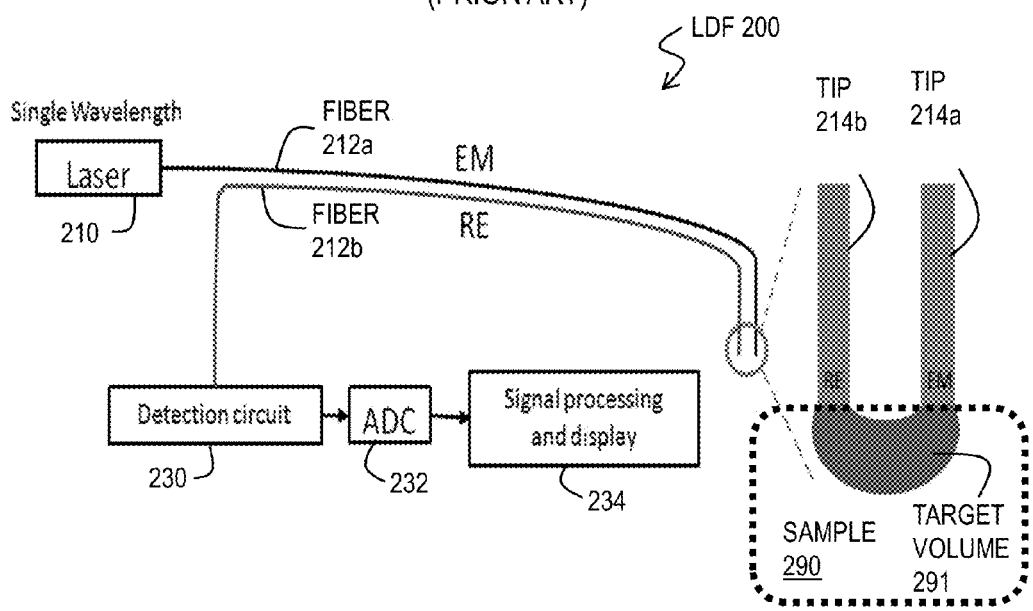
FIG. 2A is a block diagram that illustrates an example laser Doppler flowmetry (LDF) apparatus for detecting fluid flow within tissue.

FIG. 2A is a block diagram that illustrates an example laser Doppler flowmetry (LDF) apparatus 200 for detecting fluid flow within tissue. To illustrate the operation of device 200, a sample 290 is depicted; however, sample 290 is not part of apparatus 200. As used here and throughout, a sample refers to any subject on which a device operates, whether a living organism, including humans, animals and plants, or an excised portion thereof, or some other object, such as a device with moving parts, including moving fluids.

The LDF apparatus 200 includes a narrow bandwidth laser source 210 called a single wavelength laser source, light from which is coupled to optical fiber 212a that terminates in a first probe tip 214a. This light is called emitted light and is signified in FIG. 2A by the letters "EM." In practice, the laser source 210 is not absolutely single wavelength but comprises light in a very narrow wavelength band, typically with a wavelength bandwidth of about 0.08% of a center wavelength in the band or less.

The light from laser 210 exits the tip 214a and interacts with a target volume 291 of the subject 290. The target volume depends on the attenuation of the light at the single wavelength of laser 210 in the subject 290. Light propagating through or scattered from the target volume, or both, enters tip 214b of optical fiber 212b and propagates along fiber 212b from the tip to a detection circuit 230. This light propagating through fiber 212b is called returned light and is signified in FIG. 2A by the letters "RE." The detection circuit outputs an electronic signal, such as current or voltage, proportional to the electric or magnetic field that impinges on a light sensitive portion of the detection circuit 230. In the illustrated embodiment, the signal output by the detection circuit is an analog signal. That signal is passed to the analog to digital converter (ADC) 232 which outputs a digital signal that can be processed by a digital processor, as described below with reference to computer system 1500 in FIG. 15 or chip set 1600 in FIG. 16. Digital signal processing and display components 234 are configured to process the digital signal and present the results, such as a graph or listing that indicates a number or speed of scatterers in the target volume 291 for one or more speed intervals at one or more times.

The interference at the detection circuit 230, if any, is caused by a difference between the returns from scatterers in target volume 291 that are not moving and the Doppler shifted returns from moving scatterers in target volume 291. Because the same target volume 291 provides both the Doppler shifted and non-Doppler shifted optical waves (also referred to as photons, the quantum unit of electromagnetic waves), the interference pattern at the detection circuit 230 is said to be homodyne interference. While suitable for many purposes, the target volume is large compared to the features of interest (e.g., blood vessels or microchannels) in many applications. Thus the device 200 indicates whether there is motion in the volume 291 but does not indicate where in the volume the motion occurs. For example, one can determine that blood is flowing through tissue in the target volume but the blood vessels cannot be localized. Also, if there are too many background moving scatterers outside a region of interest or too few non-moving scatterers in the volume, the signal to noise ratio suffers and may render the measurements unreliable.

The target volume 291 is difficult to control because of the large coherence length Lc of the narrowband laser 210. Temporal coherence is a measure of the average correlation between the value of a wave and itself delayed by a time difference τ, at any pair of times. Temporal coherence tells how monochromatic (single wavelength) a source is. In other words, it characterizes how well a wave can interfere with itself at a different time. The delay over which the phase or amplitude wanders by a significant amount (and hence the correlation decreases by significant amount) is defined as the coherence time τc. At τ=0, the degree of coherence is perfect; whereas, it drops significantly by delay τc. The coherence length Lc is defined as the distance the wave travels in time τc. A wave with a longer coherence length is closer to a perfect sinusoidal wave. Wave interference is strong when the paths taken by all of the interfering waves differ by less than the coherence length. Thus, with the long coherence length of the narrowband light source 210, moving and non-moving scatterers throughout a large target volume 291 interfere significantly at detection circuit 230.

To better localize the vessels holding moving fluids in a sample, such as tissue of a living organism, imaging systems have been developed, which use wideband optical sources with short coherence lengths to achieve a very small and well controlled target volume. Such a small target volume is not likely to include a feature of interest, however; so, a scanning mechanism is included to scan a large number of target volumes, which can be presented as pixels or voxels in two dimensional (2D) or three dimensional (3D) images, respectively. One such imager is a DOCT device that requires a light source with a large optical bandwidth (typical bandwidth≤6% of the center wavelength), a lateral scanning and depth scanning mechanism, and a visual display.

Figure 2B:
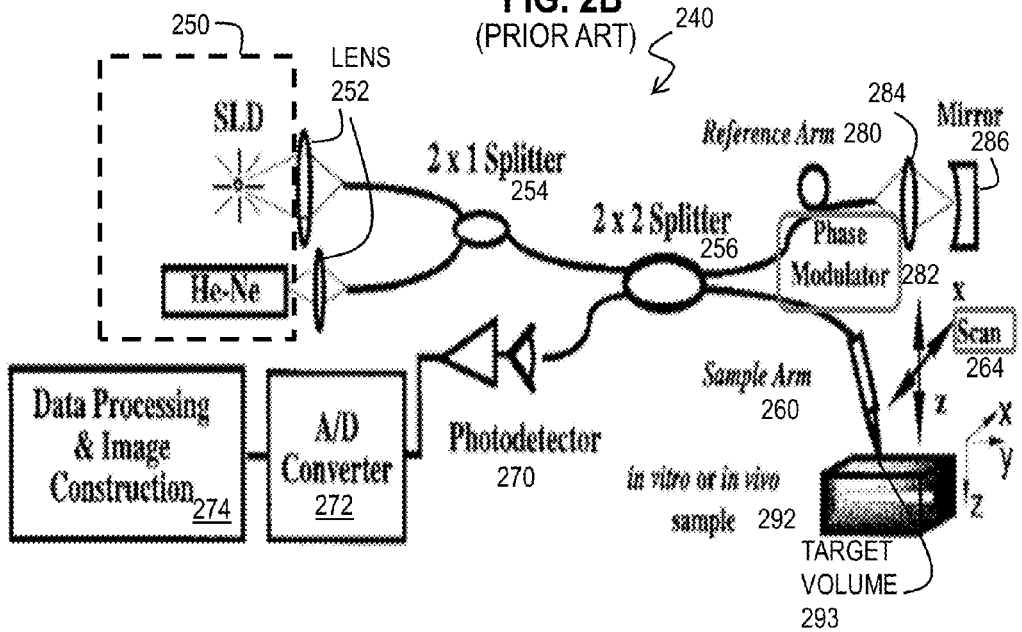
FIG. 2B is a block diagram that illustrates an example Doppler optical coherence tomography (DOCT) apparatus for producing images of fluid flow location within a tissue.

FIG. 2B is a block diagram that illustrates an example Doppler optical coherence tomography (DOCT) apparatus 240 for imaging fluid flow within tissue. This example is taken from Z. P. Chen, T. E. Milner, S. Srinivas, X. J. Wang, A. Malekafzali, M. J. C. vanGemert, and J. S. Nelson, "Noninvasive imaging of in vivo blood flow velocity using optical Doppler tomography," Optics Letters, v22, pp 1119-1121, 1997. To illustrate the operation of device 240, a sample 292 is depicted; however, sample 292 is not part of apparatus 240.

The DOCT apparatus 240 includes a wide bandwidth light source 250, such as a superluminescent diode (SLD) to produce power at the scattering frequency of red blood cells combined with a an Helium-Neon (He—Ne) laser for indicating the target volume by a position of a He—Ne laser spot. A SLD combines the high power and brightness of laser diodes with the low coherence of conventional light-emitting diodes. Its emission band is in a range from about 5 nm to about 100 nm wide. Light from this source 250 is coupled by lenses 252 and 2×1 splitter 254 and 2×2 splitter 256 to optical fiber in a sample arm 260. A probe tip at distal end of sample arm 260 directs light into a minute target volume 293 in an in vivo or in vitro sample 292. The probe tip is controlled by a scanning mechanism to scan multiple target volumes 293 in the sample 292. For example, Z. P. Chen et al. state, "Two-dimensional images are formed by sequential lateral scans at a constant horizontal velocity of 800 μm/s (micrometers, μm, also called microns, 1 μm=$10^{-6}$ meters, per second), followed by incremental probe movements (10 μm) in the vertical (axial) direction." The scattered light is returned through the same sample arm to 2×2 splitter 256 which sends a portion to photodetector 270.

Because the target volume 293 is so small, it is not likely to return sufficient numbers of Doppler shifted and non-Doppler shifted photons from moving and non-moving scatterers, respectively, for a useful homodyne interference signal. In this case a reference path is used through a reference arm optical fiber 280 to provide non-Doppler shifted photons to produce interference at photodetector 270. Because the non-Doppler shifted photons are not from the same target volume 293 as the Doppler shifted photons, if any, this type of interference is called heterodyne interference. A portion of the light from source 250 is coupled into the reference arm by 2×2 splitter 256. Because the signal from source 250 is broadband, the coherence distance is very short and to achieve significant interference at photodetector 270 the difference in the path length between the returns from the sample arm 260 and the returns from the reference arm 280 must be less than the coherence distance Lc. To match the path distances, the reference arm includes a lens 284 and a moveable mirror 286. To avoid confounding homodyne interference with the desired heterodyne interference, the reference light is changed in frequency by phase modulation component 282 so that the difference (and corresponding beat frequencies are much higher, about 8.3 kHz). The reference arm light is directed to the photodetector by 2×2 splitter 256. As stated by P. Chen et al., "Fluid-flow velocity at each pixel is determined by measurement of the Doppler frequency shift, which is defined as the difference between the carrier frequency established by the optical phase modulation and the centroid of the measured power spectrum at each pixel."

The photodetector 270 outputs an electronic signal, such as current or voltage, proportional to the electric or magnetic field that impinges on the photodetector 270. In the illustrated embodiment, the signal output by the photodetector 270 is an analog signal. That signal is passed to the analog to digital converter (ADC) 272 which outputs a digital signal that can be processed by a digital processor. Digital signal processing and image construction components 274 are configured to process the digital signal and present the results, such as an image of the locations and amounts of fluid motion, or statistics of same.

While suitable for many purposes, a DOCT is not suitable as a real-time guidance device. It is large, cumbersome, complicated, expensive and slow compared to desired motion sensing feedback that a medical practitioner, such as a surgeon, demands while operating on a living organism when executing various procedures, such as cutting, injecting or implanting functions, in or near blood vessels and vessels of other bodily fluids. With an adjustable mirror in reference arm 280, the device requires complex control and calibration and is subject to orientation changes, movement and vibration.

1. OVERVIEW

It is desired to produce a motion sensor that is suitable as a real-time guidance device for medical and other applications. Laser Doppler flowmetry (LDF) has been used in many medical procedures. However, the resolution (from several millimeters, mm, 1 mm=$10^{-3}$ meters, to about 1 centimeter, cm, 1 cm=$10^{-2}$ meters) of the two fiber design in a conventional LDF system is too coarse to enable localization and avoidance of fluid carrying vessels. Also the two fiber design with wide separation in LDF system is not compatible with minimally invasive tools. In contrast, Doppler optical coherence tomography (DOCT) creates a very small imaging spot (about 10 μm) with a single fiber. By scanning this spot, the flow information in the region of interest (ROI) can be mapped out with great resolution. However, in many clinical applications, it is not necessary to obtain high resolution images of blood vessels or to accept the tradeoffs associated with imaging, such as larger probe size, complicated and expensive system components. Often what is needed is simply to determine whether there is a blood flow at a precise location in front of a surgical probe. The techniques presented herein serve in such situations.

Figure 3A:
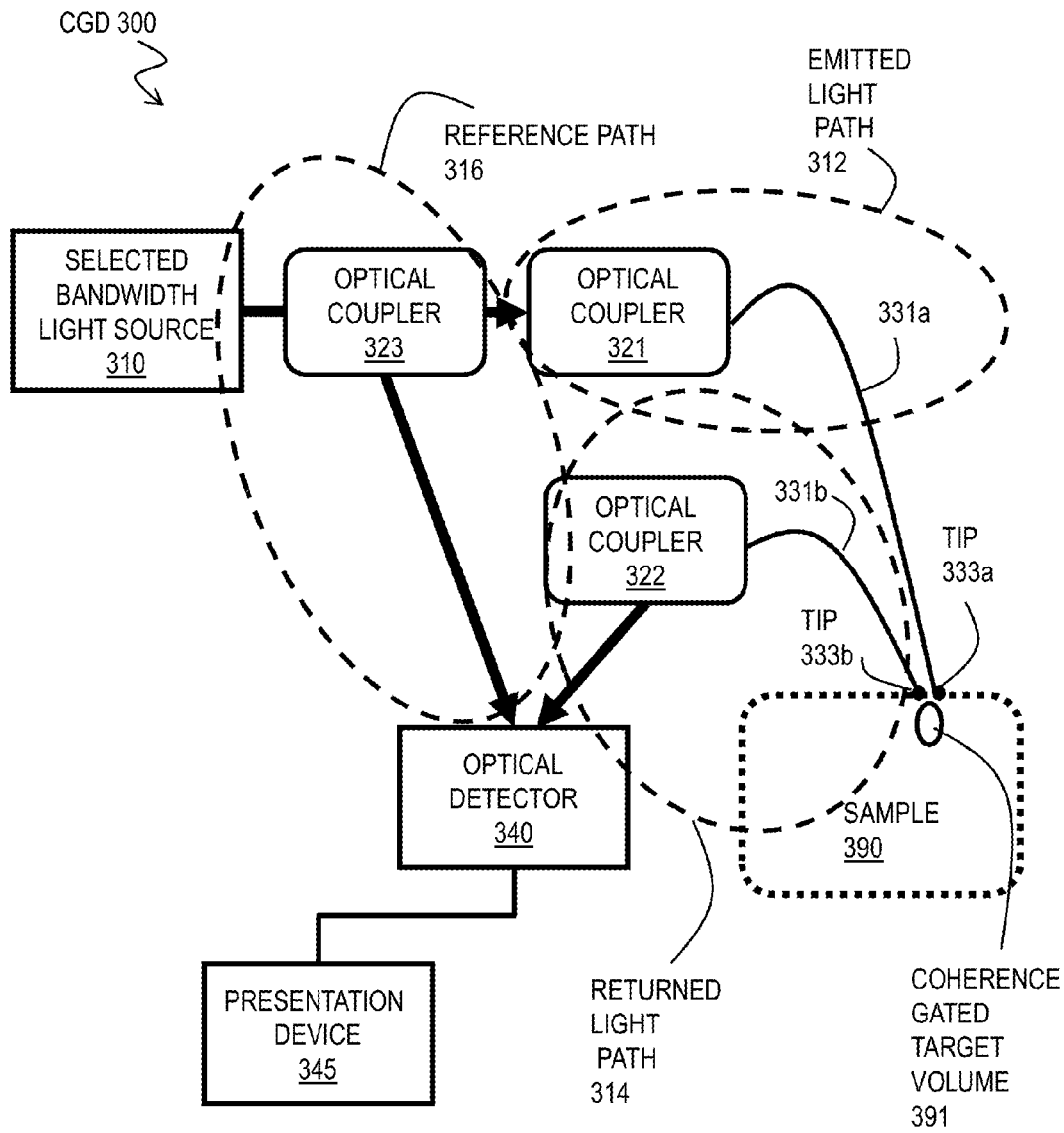
FIG. 3A is a block diagram that illustrates example components of a coherence gated Doppler (CGD) apparatus, according to various embodiments.

FIG. 3A is a block diagram that illustrates example components of a coherence gated Doppler (CGD) apparatus 300, according to various embodiments. To illustrate the operation of device 300, a sample 390 is depicted; however, sample 390 is not part of apparatus 300.

CGD device 300 includes a selected bandwidth light source 310 that determines both a center wavelength in order to appropriately penetrate a sample 390 and detect scatterers that move with the motion to be detected, and also the coherence length Lc appropriate for a target volume appropriate for the application. For example, for a hand-held probe, an appropriate target volume is on the order of a cubic millimeter, such as volumes with spot diameters in a range from about 0.1 millimeters (100 microns) to about 5 millimeters. A surgical hand held probe fits in the palm of one hand, weighs about a pound or less, and is robust in the presence of involuntary hand motions of the surgeon or assistant, e.g., robust in the presence of motions of about millimeter over a tenth of a second. Horizontal diameter can be affected by focusing, and can go down to about 40 μm and further down to submicrons, but the vertical extent of the coherence gated target volume 391, and hence the volume at least in part, is determined by the coherence length Lc. For such spot depths a wavelength bandwidth of about 3 nm is advantageous. For blood cell scatterers, a center wavelength of about 1300 nm is desirable, and the 3 nm bandwidth corresponds to about 0.2% of the center wavelength. For a shorter center wavelength, the percentage is higher. For many applications, it is advantageous for the bandwidth to be intermediate between that of LDF and DOCT, e.g., for bandwidths in a range from about 0.1% to about 5% of a center wavelength. In some applications, it is preferable for the bandwidth to be in a range from about 0.2% to about 3%. In embodiments directed to the detection of blood cells, it is desirable for the bandwidth to be in a range from about 0.4% to about 0.8%. Because the target volume 391 is controlled, at least in part, by the coherence length of the source 310, the volume 391 is called a coherence gated target volume 391 and the device 300 is called a coherence gated Doppler (CGD) device.

The present system is designed to increase light penetration and to control the size and location of the detection zone. Different types of light sources having various wavelengths may be used. Suitable light sources with selected center wavelength and bandwidth are known in the art. In one embodiment for application to teeth, a Superluminescent Light Emitting Diodes light source (SLED) with a center wavelength of about 1300 nm is used. This differs significantly from a conventional laser Doppler's wavelength of 780 nm because the teeth will not attenuate the longer wavelength infrared light as much. The SLED is also a preferred embodiment because it has a special type of laser diode with wider spectral bandwidth. As stated above, the bandwidth controls the "coherence length" which in turn controls the detection volume. Besides SLED, it is also possible to use a white light laser with suitable bandpass filter or semiconductor laser with appropriate bandwidth.

The device also includes an optical detector 340 that outputs an electronic signal, such as a digital or analog current or voltage, which indicates the optical interference pattern at the detector. Example detectors include a photodiode, an Indium gallium arsenide (InGaAs) photodetector, a balanced detector, a charge-coupled device (CCD) and a Complementary metal-oxide-semiconductor (CMOS) photodetector. In some embodiments, a dual balanced detection circuit from Thorlabs, Newton, N.J. is employed as detector 340 to improve signal to noise ratio by reducing common mode noise.

The light from source 310 is directed into an emission path 331a which terminates at a distal end in a probe tip 333a. In various embodiments, the probe tip 333a is a simple perpendicular cut of an optical fiber serving as emission path 331a, or an angled cut of the fiber serving as emission path 331a to control the back reflection power from the end surface, or a shaped end of the fiber to control the back reflection power from the end surface, or a coated end surface of the fiber to control the back reflection power from the end surface, or a Gradient-index (GRIN) multimode fiber to serve as a lens, or a GRIN rod lens, or ball lens, or a micro-lensed fiber or is a stiff needle connected to the emission path 331a, or includes a lens or collimator, or a coating or other optical coupler, or some combination. The probe tip is configured to emit light from source 310 and direct it onto a spot in or on the sample 390. In various embodiments, a fiber of emission path 331a is a single mode optical fiber which propagates light received in a particular direction or a multimode optical fiber which propagates light received in multiple directions, or some combination. In some embodiments, the probe tip 333a is configured to be held in a hand of a user.

An optical coupler 321 is configured to couple light received directly or indirectly (e.g., through optical coupler 323) from the source 310 into the emission path 331a. As used herein the term optical coupler refers to any components or configuration of components that serve to direct light from one region (point, area or volume) of space to another region of space, and includes, among others, a free space vacuum, a gas or liquid filled free space, a crystal, a lens, Gradient-index (GRIN) optical component, such as a GRIN lens, a fiber bundle, a fiber coupler (FC), a beam splitter, a circulator, an optical fiber, a mirror, or any combination. Optical coupler 321, emission path 331a and tip 333a comprise an emitted light path 312 indicated by dashed oval in FIG. 3A.

A return path 314 terminates at a distal end in in a probe tip 333b. The light returned from sample 390 is captured at probe tip 333b and directed into the return path fiber 331b. As is the case for probe tip 333a, in various embodiments, the probe tip 333b can take various forms. In some embodiments, the probe tip 333b is configured to be held in a hand of a user. It is advantageous if the probe tip 333b and probe tip 333a are configured to be held together, e.g, by fixing one to the other. In various embodiments, the optical fiber 331b of return path 314 is a single mode optical fiber or a multi-mode optical fiber or some combination. The return path 314 is configured to capture light from the probe tip 333b and direct it directly or indirectly (e.g., through optical coupler 322) to the optical detector 340. Optical coupler 322, fiber 331b and probe tip 333b comprise a returned light path 314 indicated by dashed oval in FIG. 3A.

In some embodiments, a single optical fiber (hereinafter called optical fiber 331) serves as both emission path fiber 331a to direct light from source 310 onto the sample 390 through tip 333a and return path fiber 331b to capture light from the sample 390 through the tip 333b and direct it to the optical detector 340. In some of these embodiments, the probe tip 333a is the same as probe tip 333b, referenced hereinafter as probe tip 333. In some embodiments, probe tip 333 is configured to be held in a hand of a user.

An optical coupler 322 is configured to couple light received from the return path fiber 331b to optical detector 340. In various embodiments, optical coupler 322 includes any components or configuration of components that are suitable to this function.

In some embodiments, homodyne interference is relied upon and the returned light directed to detector 340 creates a useable interference pattern. In some embodiments, heterodyne interference is utilized and a reference path is introduced to direct light from the source 310 onto optical detector 340. In such embodiments, optical coupler 323 is included to direct light from the source 310 to the optical detector 340. Optical coupler 323, comprises a reference light path 316 indicated by dashed oval in FIG. 3A. The configuration of the fiber couplers of the systems depend on the purpose of the system. Variations in the distribution of the laser power between the emitted light path and the reference path will be application specific. In one example embodiment, the fiber coupler 323 distributes 10% of laser power to the reference path 316 and the other 90% to the emitted light path 312. In other example embodiments, the laser power distributed to the probe can be between about 99% and about 1%. For medical use, the preferred power expelled by the probe tip 333a should not exceed the United States Food and Drug Administration (FDA) recommendation. The optical probe tip 333a is capable of focusing the laser beam in a perpendicular direction at different sizes. In one example, the beam is focused to a spot size of 40 μm at a distance 1.5 mm away from the probe. However, in other uses, the spot size and distance may be more or less. The size of the target volume in the axial direction of propagation is at least in part determined, as described, above, by the coherence length Lc.

In some embodiments, optical coupler 323 includes a path length correction component so that a zero delay plane can be placed at the region of interest within the sample 390. The zero-delay plane is defined as the plane in the sample which has same optical path length to detector as the reference path. Since the signal from the region (defined by the coherence length Lc) surrounding the zero-delay plan is higher than signal from other regions, the position of the zero-delay plane can be set by the reference path length to highlight the region of interest within the sample 390. In some embodiments, the reference path length correction is adjustable so that the depth within the sample can be adjusted. In a preferred embodiment, the path is preset for a predetermined depth within the sample. This embodiment is advantageous because the user does not have to make the adjustment, which renders the device simpler to use and frees the user's hands for other actions. Furthermore, the mechanism to adjust the path length can be omitted, making the device more stable, less susceptible to vibration or orientation, smaller, lighter, and cheaper to build.

In some embodiments, optical coupler 323 includes phase modulation (PM) to separate homodyne from heterodyne interference. A homodyne signal comes from the interference between Doppler-shifted and non-shifted photons from within the sample. This could happen in any place within the light illumination path. The heterodyne signal comes from non-shifted reference photons and shifted sample photons within the coherence length. This signal only comes from certain sample regions with moving scatters. Heterodyne and homodyne signals are usually mixed together. In certain embodiments, such as pulp vitality, only the heterodyne signal from the pulp region may be desired and the homodyne signal from surrounding tissues should be rejected. In some systems that are configured for these applications, the heterodyne and homodyne signals are separated by introducing phase modulation to the reference arm. Said phase modulation shifts the heterodyne signal to a higher frequency and separate it from the low frequency homodyne signal. This technique may improve the specificity by reducing the background noise, but it may render the interference frequency too high for audible output from a speaker, as described below for certain embodiments.

In preferred embodiments, the phase modulation is omitted and no attempt is made to distinguish the homodyne from the heterodyne interference. Therefore all the Doppler signals accumulated in the illuminate path are received instead of just collecting the signal surrounding the zero-delay plane. This method effectively expands the detection volume, for example, expands the volume diameter from 0.2 mm to 3 mm in brain tissue.

Electronic output from detector 340 is passed to a presentation device 345 that indicates to a user the motion (amount of scatterers, speed of scatterers, or direction of scatterers, or some combination) in a coherence gated target volume 391 of sample 390. Any presentation device may be used. In some embodiments, the presentation device includes a digital port with digital output based on the electronic signal from optical detector 340, which digital output may be used by a computer system to display or speak one or more values that characterize the motion in target volume 391. In some embodiments, the presentation device is an acoustic speaker that emits an acoustic signal that depends on the output of optical detector 340.

In some of these embodiments, the optical interference signal at optical detector 340 has high amplitudes in frequencies between about 20 Hz and 20,000 Hz, and an analog output from the optical detector 240 can directly drive acoustic speakers without the need for intervening significant processing or an intervening analog to digital converter (ADC). Acoustic output by the speakers in this frequency range is audible to most humans. This enables the user to hear the difference in velocity as hand held probe tips 333a and 333b are moved across the sample. Vessels associated with moving fluid can be associated with visual features determined while the user's eyes are trained on the sample 390. This makes such embodiments suitable for real time guidance while keeping the device 300 light, simple and inexpensive, compared to both LDF and, especially, DOCT devices.

In some embodiments direction of flow is inferred by rotating the probe tip in the vicinity of the sample. As the probe tip encounters more of the approaching flow, the frequency should increase; and, conversely as the probe tip encounters more of a receding flow the frequency should decrease. Thus, a direction of flow can be determined, at least qualitatively, by the dependence of frequency detected on the angle of the probe tip.

Some combinations of features described above reduce cost and improve sensitivity enough to allow detection of flow in blood vessels of various sizes using a handheld probe with no moving parts. In various embodiments, CGD is also less dependent on the relative angle between the probe and the blood vessel because, unlike conventional Doppler flow imaging, interference over long optical paths generates fluctuating speckle patterns that can be detected audibly even when vessels are probed at a 90 degree angle.

There are a number of applications that would benefit from the system described herein. The improvements outlined above, in various embodiments, enable the applications of CGD to detection of blood vessels during instrument insertion for stereotactic neurosurgery; detection and avoidance of large blood vessels during anesthesia injection, catheterization, cerebrospinal fluid collection procedures, intravascular interventions or non-vascular interventions, vessel avoidance in the brain during deep brain electrode placement, tooth pulp vitality detection (with rejection of adjacent flow in the gums), and verification of flow cessation in ligated vessels during open surgical procedures.

These devices and systems are not limited to medical use. The sensors may be designed to be used with engines or other instruments, such as microfluidic devices and micro-electro-mechanical systems (MEMS), where it is important to monitor or detect flow.

2. EXAMPLE EMBODIMENTS

Figure 3B:
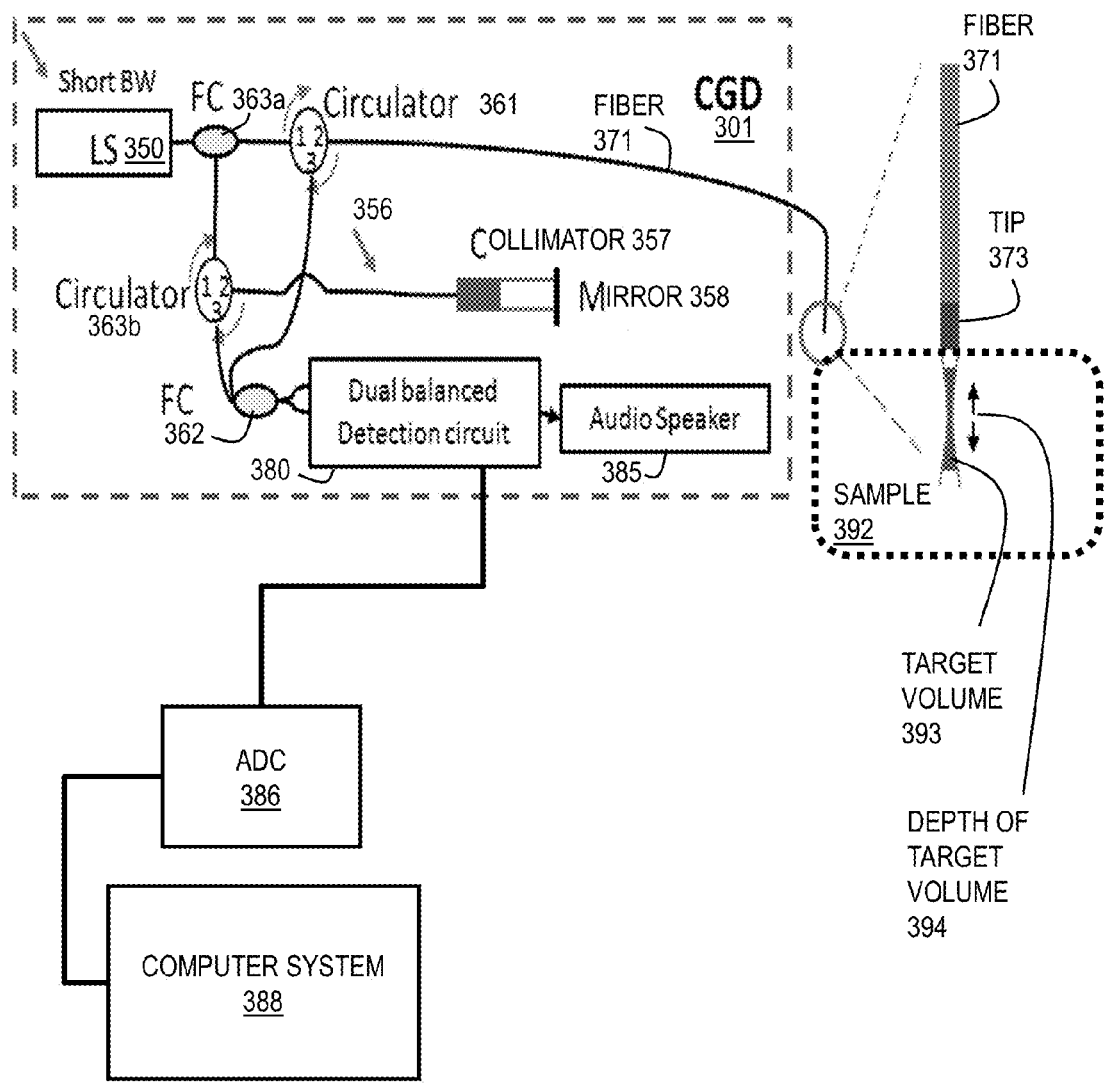
FIG. 3B is a block diagram that illustrates an example CGD apparatus, according to one embodiment.

FIG. 3B is a block diagram that illustrates an example CGD apparatus 301, according to one embodiment. To illustrate the operation of device 301, a sample 392 is depicted; however, sample 392 is not part of apparatus 301. In this embodiment, the optical source 350 has a short bandwidth compared to a DOCT light source, and there is a single optical fiber 371 and probe tip 373 (corresponding to single optical fiber in a single emission path 331 and single probe tip 333, respectively, described above with reference to FIG. 3A). The optical coupler 321 of FIG. 3A to direct light into optical fiber 371 includes circulator 361, which receives light from the source 350 on port 1 and outputs that light at port 2 as the emitted light traveling to the probe tip 373, where it illuminates target volume 393 in sample 392 centered at a depth 394. The arrows at depth 394 indicate the depth is adjustable depending on a mirror in path length correction components of a reference path, as described above.

The optical coupler 322 of FIG. 3A to direct light onto a detector includes circulator 361, which receives light from the sample 392 on port 2 and outputs that light at port 3. The optical coupler 322 also includes fiber coupler (FC) 362 to direct a portion of that light on to each of two optical detectors in dual balanced detection circuit 380 that serves as detector 340 of FIG. 3A. In some embodiments, the circuit 380 further amplifies and filters the interference signal.

The optical coupler 323 in the reference path of FIG. 3A includes FC 363a, circulator 363b, and path correction arm 356. FC 363a couples the light from the source 350 to both the circulator 361 in the emitted light path and the circulator 363b in the reference path. In other embodiments a splitter is used that sends different fractions of the source light intensity on the different paths, such as 90% of the light to the emitted light path to account for intensity loss by absorption and scattering in the sample 392. The circulator 363b directs that light onto path length correction arm 356 with collimator 357 and mirror 358. In other embodiments, other reflective or partially reflective surfaces are used instead of mirror 358. The light returning from the correction path to port 2 of circulator 363b is output on port 3 to FC 362 and thence to detectors of the dual balanced detection circuit 380. In some embodiments, the position of mirror 385 is adjustable to adjust the reference path length and, thus, the depth in sample 393 that is coherent with the reference signal on the reference path. In a preferred embodiment, a smaller, cheaper more reliable device 301 is produced by fixing the position of mirror 358, and thus fixing the depth 394 of the target volume.

The presentation device 345 of FIG. 3A includes the audio speaker 385, as described above. In some embodiments, the presentation device 345 includes, in addition to or instead of speaker 385, electrical output to ADC 386, or the ADC 386 or a computer system 388, such as system 1500 described in more detail below with reference to FIG. 15, which presents data on a display, or some combination. In some embodiments, one or more functions of computer system 388 are performed by a chip set 1600 as depicted in FIG. 16. In some embodiments, the ADC is a data acquisition card (DAQ), which is an application specific integrated circuit (ASIC) of computer system 1500.

Figure 4:
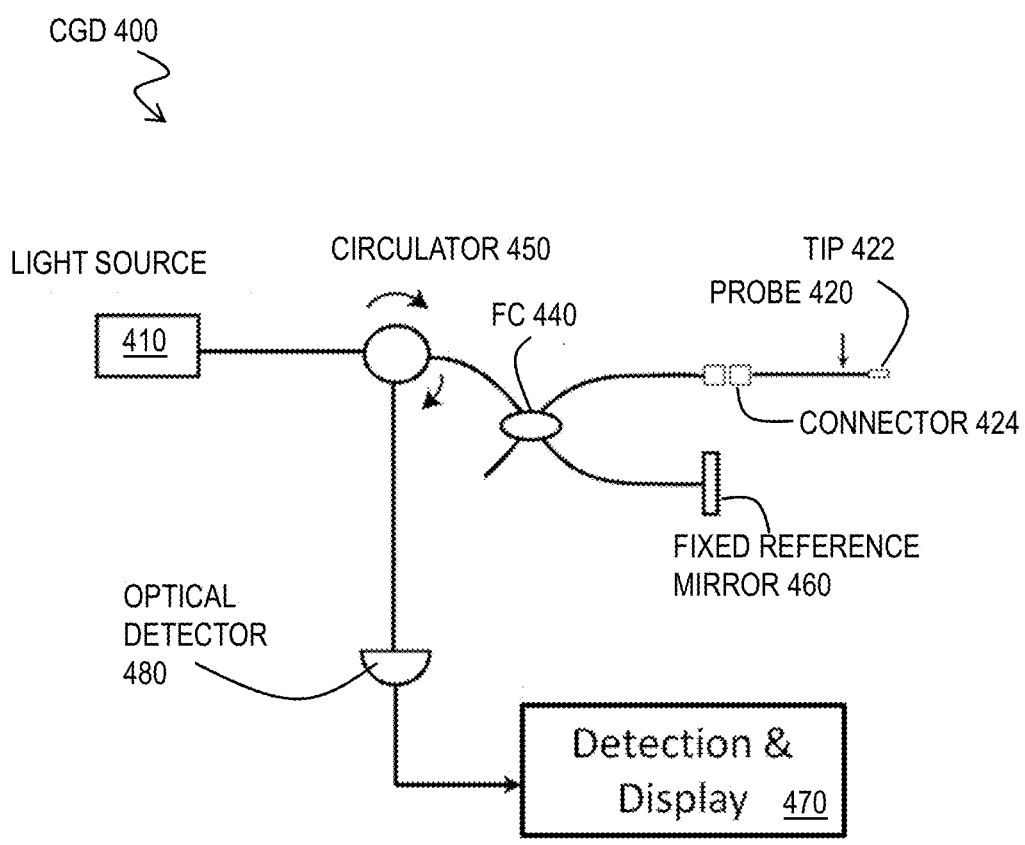
FIG. 4 is a block diagram that illustrates an example CGD apparatus, according to another embodiment.

FIG. 4 is a block diagram that illustrates an example CGD apparatus 400, according to another embodiment. Device 400 is simpler than device 301 of FIG. 3B, and is useful when sensitivity is not as important. Device 400 comprises light source 410, optical probe 420, fiber coupler 440, circulator 450, fixed reference mirror 460, detection and display component 470, and light detector 480. Light source 410 is configured to transmit light to circulator 450. Port 1 of circulator 450 receives the light and channels the light through port 2 to fiber coupler 440. Fiber coupler 440 is connected to optical probe 420 and fixed reference mirror 460. Fiber coupler 440 is configured to receive backscattering light from probe 420 and mirror 460 and allow both to channel back to port 2 of circulator 450. Port 2 of circulator 450 directs the backscattered and reference light through port 3 to light detector 480. Light detector 480 outputs an electronic signal based on the optical interference to the detection and display 470. A dual balance detection circuit is not used. Otherwise, the detection and display 470 is similar to that of the device 301 described with reference to FIG. 3B for various embodiments.

Figure 5:
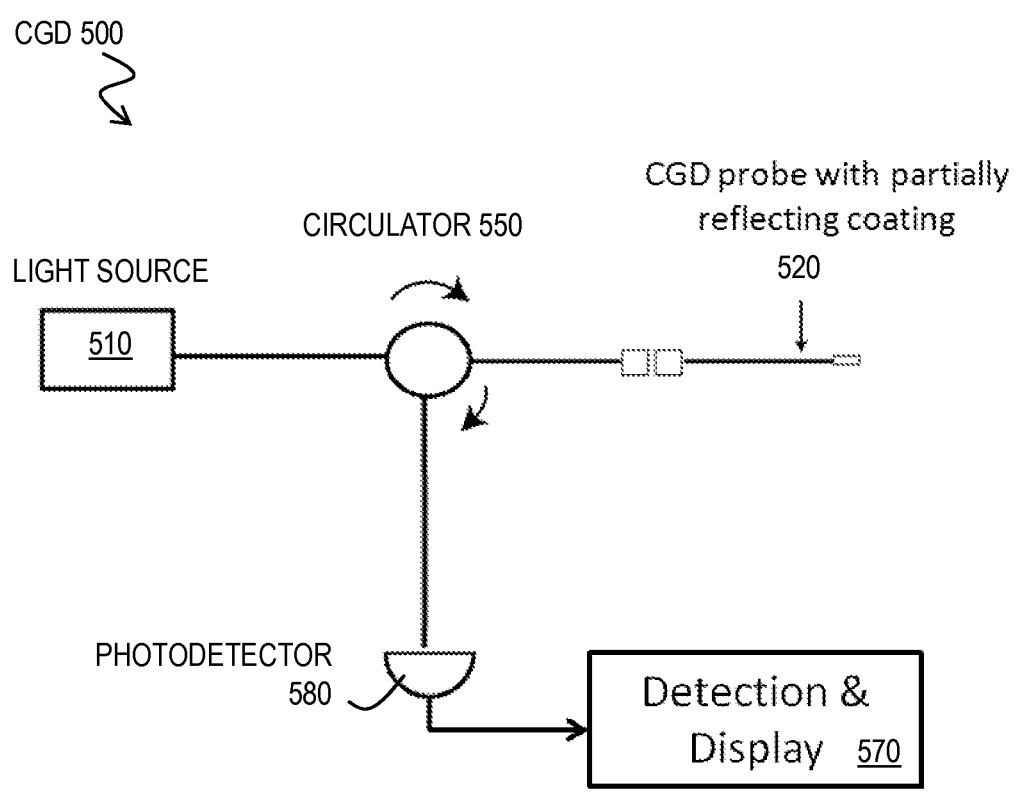
FIG. 5 is a block diagram that illustrates an example CGD apparatus, according to yet another embodiment.

FIG. 5 is a block diagram that illustrates an example CGD apparatus 500, according to yet another embodiment. In this embodiment, an independent reference arm is not used to generate the interference signal. Instead, a reflector is integrated into the optical probe tip. Here, light source 510 transmits light through port 1 of circulator 550. Port 2 passes the light to probe 520. Probe 520 has a partial reflective surface which serves as a reference. Port 2 of circulator 550 receives the backscattered light from the target and the reference light from the reflective surface and outputs the interfering light through port 3. Port 3 passes the interfering light to photodetector 580. Photodetector 580 outputs an electronic signal to detection and display component 570, which presents the signal according to one of the embodiments described above.

Figure 6:
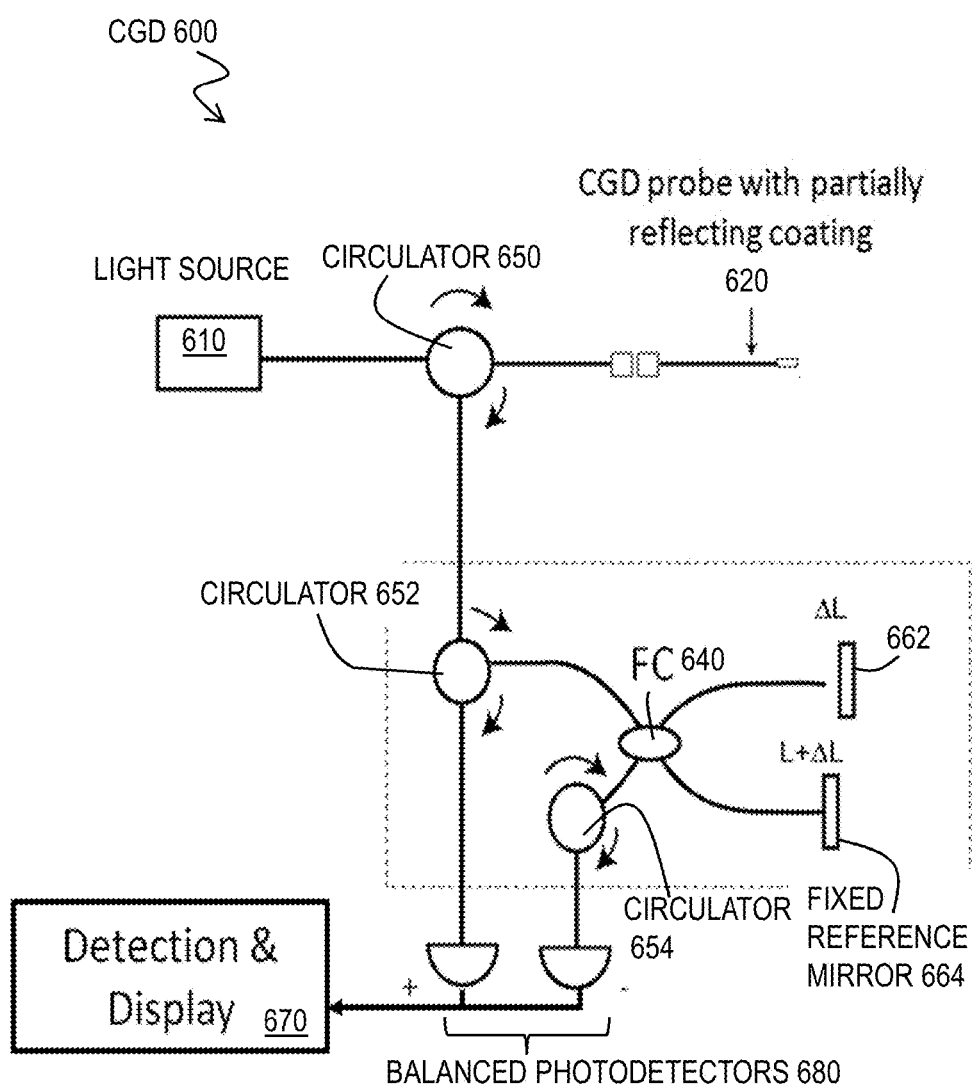
FIG. 6 is a block diagram that illustrates an example CGD apparatus, according to still another embodiment.

FIG. 6 is a block diagram that illustrates an example CGD apparatus 600, according to still another embodiment. This embodiment includes a second interferometer for controlling a center position of the target volume, and a high-sensitivity dual balanced detection circuit. Device 600 has a light source 610, circulator 650, and probe tip 620 corresponding to light source 510, circulator 550 and probe tip 520 described in FIG. 5. However, port 3 of circulator 650 channels the backscattered and reference light from probe 620 to a circulator 652. Port one of circulator 652 receives the light and passes it through port 2 to fiber coupler 640. Fiber coupler 640 is configured to receive the light and transmit it to fixed reference mirror 662 and fixed reference mirror 664. Fixed reference mirrors 662 and 664 must have different known lengths. The backscattered and reference light from fixed reference mirrors 662 and 664 is reflected back through fiber coupler 640. The light is then received by port two of circulators 652 and 654 and channeled through port 3 to balanced photodetectors 680. Balanced photodetectors output an electronic signal to detection and display 670 which works as the detection and displays described above. Even though the second interferometer is depicted in FIG. 6 to be used with the probe tip of FIG. 5, it is noted that, in other embodiments, this second interferometer is used with any other components described herein.

Figure 7:
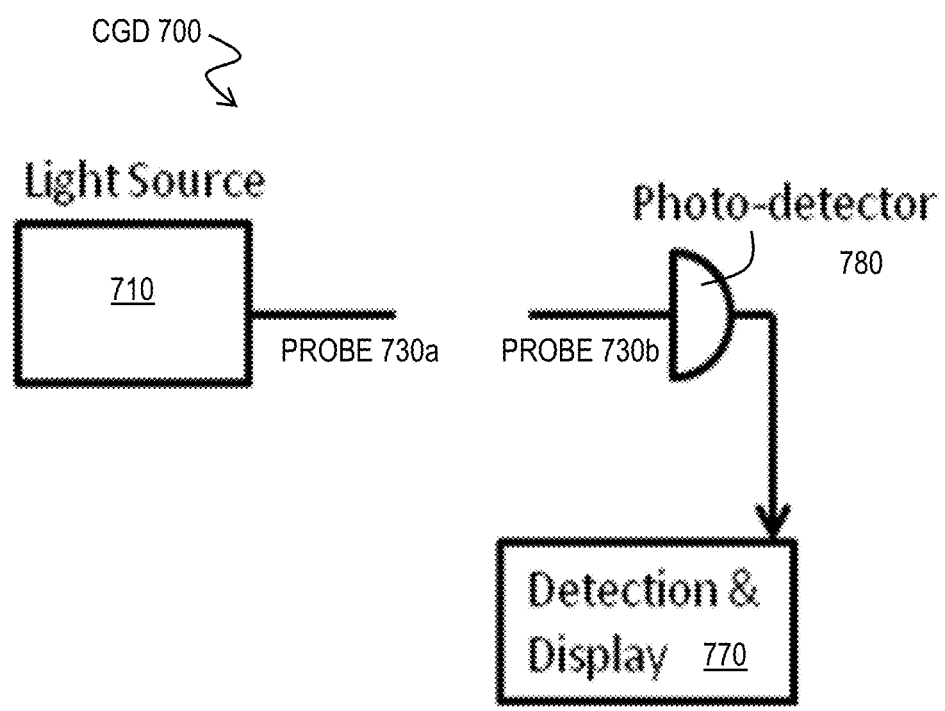
FIG. 7 is a block diagram that illustrates an example CGD apparatus, according to a yet further embodiment.

FIG. 7 is a block diagram that illustrates an example CGD apparatus, according to a yet further embodiment. This apparatus uses separate fibers and probes, as depicted in FIG. 3A as fibers or path 331a and path 331b and probe tips 333a and 333b, respectively. Apparatus 700 includes a light source 710, two optical probes 730a and 730b (each comprising an optical fiber and probe tip), a photodetector 780, and detection and display component 770. From the source 710, the light is coupled into one optical probe 730a which is used to illuminate the sample. Another probe 730b is then used to collect the transmitted light through the sample. This set up only records the self-interference photons (homodyne interference) with path lengths in the limited coherent range of the limited bandwidth light source, compared to a LDF system. The transmission mode of apparatus 700 provides better sensitivity than the reflection mode system in some embodiments, while still providing the higher resolution target volume of the other CGD devices.

Figure 8:
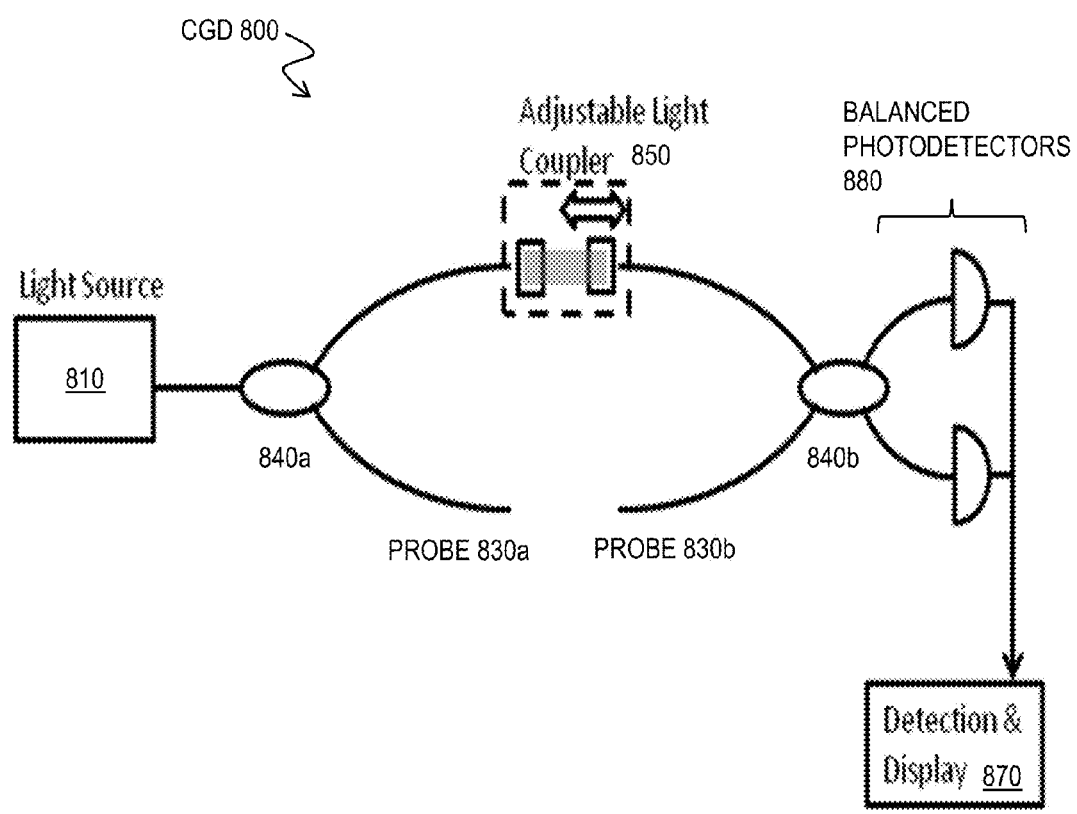
FIG. 8 is a block diagram that illustrates an example CGD apparatus, according to yet a still further other embodiment.

FIG. 8 is a block diagram that illustrates an example CGD apparatus 800, according to yet a still further other embodiment. Device 800 includes a light source 810, two optical probes 830a and 830b, two fiber couplers 840a and 840b, an adjustable light coupler 850 with two lenses, balanced photodetectors 880, and detection and display component 870. The light from the source 810 is coupled into the fiber coupler 840a. From fiber coupler 840a part of the light goes to the optical probe 830a and illuminates the sample while another part is collimated with a first lens in adjustable light coupler 850. The distance between the two lenses of adjustable light coupler 850 is adjustable for eliminating the diffuse background noise. From the sample, the transmitted light is collected with optical probe 830b and is directed into the coupler 840b. The collimated light from the adjustable light coupler 850 is also directed into coupler 840b to generate the interference signal. Then, the interference signal is acquired by the balanced photodetectors 880 and processed by the detection and display component 870. In homodyne embodiments, the reference optical path through coupler 850 passes through a portion of the sample.

3. EXAMPLE MEDICAL APPLICATION EMBODIMENTS

Ex Vivo Human Tooth Pulp Dentin Boundary.

Figure 9A:
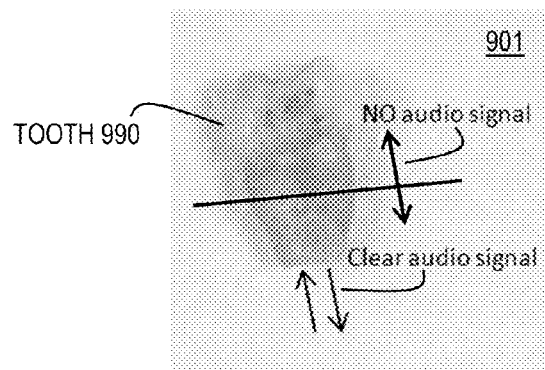
FIG. 9A is an image that illustrates an example application of a CGD apparatus, according to an embodiment.

FIG. 9A is an image 901 that illustrates an example application of a CGD apparatus, according to an embodiment. Here an embodiment of the device 400 depicted in FIG. 4 was used to measure flow through an ex vivo human tooth 990. A laser diode light source with a wavelength of 1300 nm and a bandwidth of 3 nm was selected. The optical fiber circulator 450 sent the illumination light from port 1 to port 2 and the backscattered and reference light from port 2 to port 3. The fiber coupler (FC) 440 distributed 10% of laser power to the reference arm and other 90% to the optical fiber probe (ImageWire™ from LightLab Imaging Inc. of Westford, Mass.). Thus, 5 milliwatts (mW, 1 mW=$10^{-3}$ watts) laser power were delivered onto the sample. The optical fiber probe tip 420 focused the laser beam to a spot size of 40 μm at the distance 1.5 mm away from the probe. When the probe contacted the teeth, the beam waist was roughly at the junction between dentin and pulp. The backscattering photons from the sample were combined with the photons reflected from the fixed reference mirror to generate the interference pattern.

Since the sample photons which have traveled through an optical path length (OPL) almost identical to an OPL of reference photons (offset no larger than the coherence length Lc of about 0.2 mm) generate most of the interference signal, a depth of the detection volume can be preset to an appropriate depth by setting the position of reference mirror. The photodiode and detection circuit then converted the interference signal to an electronic signal. After amplification and noise filtering, but no ADC, the speaker converted the electronic signal to an acoustic (audio) signal and the laptop recorded and analyzed the signal through a data acquisition (DAQ) card.

Since the frequency of interference signal is proportional to the flow speed and within the human audio spectrum (20 to 20,000 Hz), the audio feedback allows operators to easily acquire qualitative measurement without being distracted by looking at the signal on a remote screen. Alternatively, the flow speed could be quantitatively measured by analyzing the power spectrum of interference signal. The total weight, excluding the laptop, is below 2 kilograms (kg, 1 kg=$10^3$ grams).

Figure 9B:
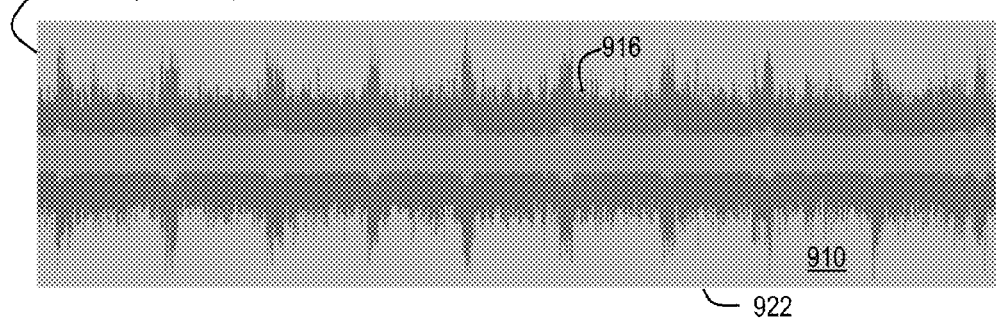
FIG. 9B through FIG. 9C are graphs that illustrate results of the application of FIG. 9A, according to an embodiment.
Figure 9C:
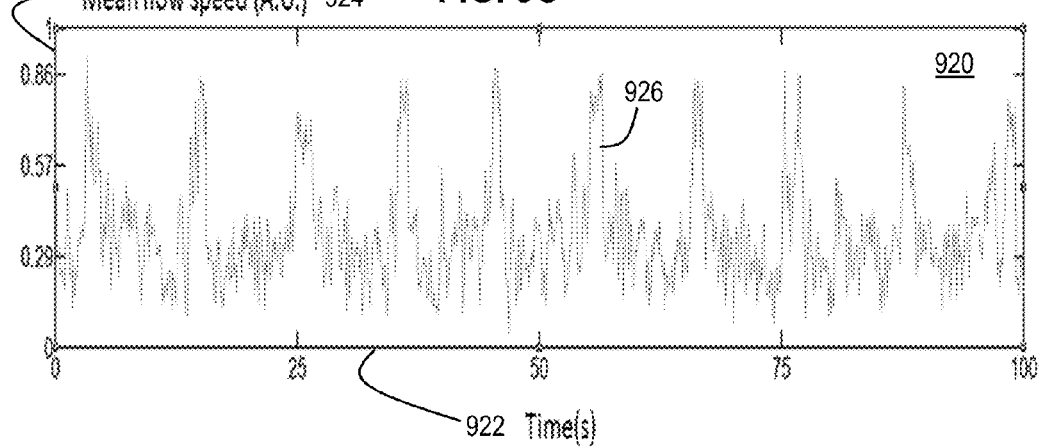

The sensitivity of the system described above was tested on an extracted human premolar tooth with simulated blood pulsation, generated by intermediate injection of 2% intralipid solution at a perfusion rate of 0.067 milliliters per second (ml/s, 1 ml=$10^{-3}$ liters). FIG. 9B through FIG. 9C are graphs 910 and 920 that illustrate results of the application of FIG. 9A, according to an embodiment. The horizontal axis 922 for both indicates time in seconds. The vertical axis 912 of graph 910 indicates audio signal strength in volts driving the audio speaker. Trace 916 shows the signal as a function of time. The vertical axis 922 of graph 920 indicates mean flow speed in arbitrary units. Trace 926 shows the flow speed as a function of time.

The audio signal trace 916 recorded by a voice recorder has very similar pattern to the quantitative flow speed measurement of trace 926, which validates using the audio signal to indicate the flow pattern. When the flow speed was elevated by injection, both amplitude and frequency of audio signal 916 increased and the pulsation pattern could be easily recognized by the human ear. The data displayed was acquired from the apical part of the tooth root as indicated in FIG. 9A.

In Vivo Rat Femoral Vessel Blood Flow Measurement

Figure 10A:
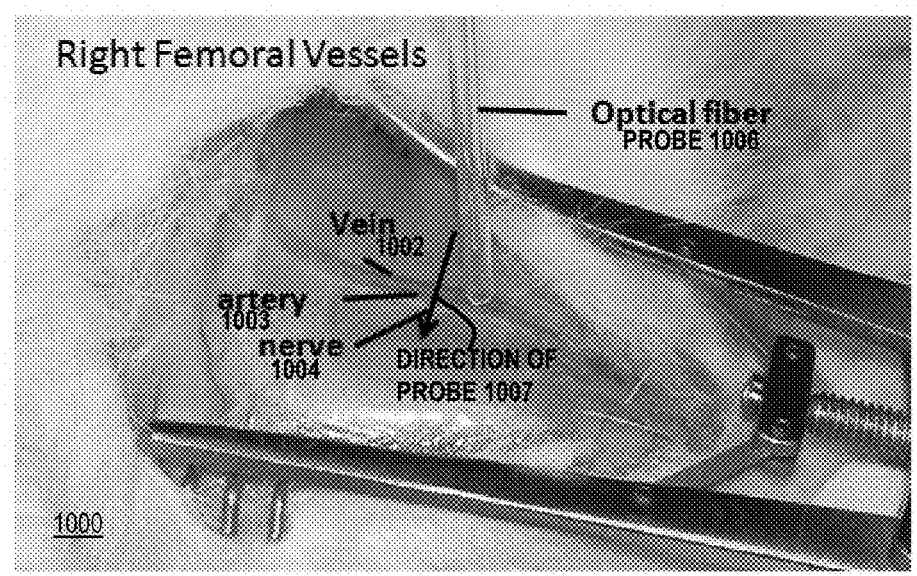
FIG. 10A is an image that illustrates an example application of a CGD apparatus, according to another embodiment.

FIG. 10A is an image 1000 that illustrates an example application of a CGD apparatus, according to another embodiment. Image 1000 depicts right femoral vessels of a rat. Evident are features identified as vein 1002, artery 1003 and nerve 1004 to be distinguished by their motion signatures. Just like a conventional laser Doppler system, the frequency of interference signal is in the audible acoustic (audio) frequency range and represents the flow speed of the scatterers (red blood cells), while the amplitude represents the quantity (amount) of scatterers. Therefore, if the time-domain audio signal is transformed to the frequency domain, the amount of scatterers in a specific flow speed can be measured. From the flow speed histogram, the mean flow speed of scatterers in a target detection volume can be measured. The integration time of flow speed measurement is 0.1 seconds (10 Hz) for the example embodiment device of FIG. 4. This integration time is fast enough to observe the rapid rat heart beat (about 5 Hz).

FIG. 10A shows the CGD probe placed above rat femoral vessels. The optical probe 1006 is protected in transparent plastic tubing and the sample is placed 3 mm away from the probe tip. The probe was moved in direction 1007 to acquire the information from different locations.

Figure 10B:
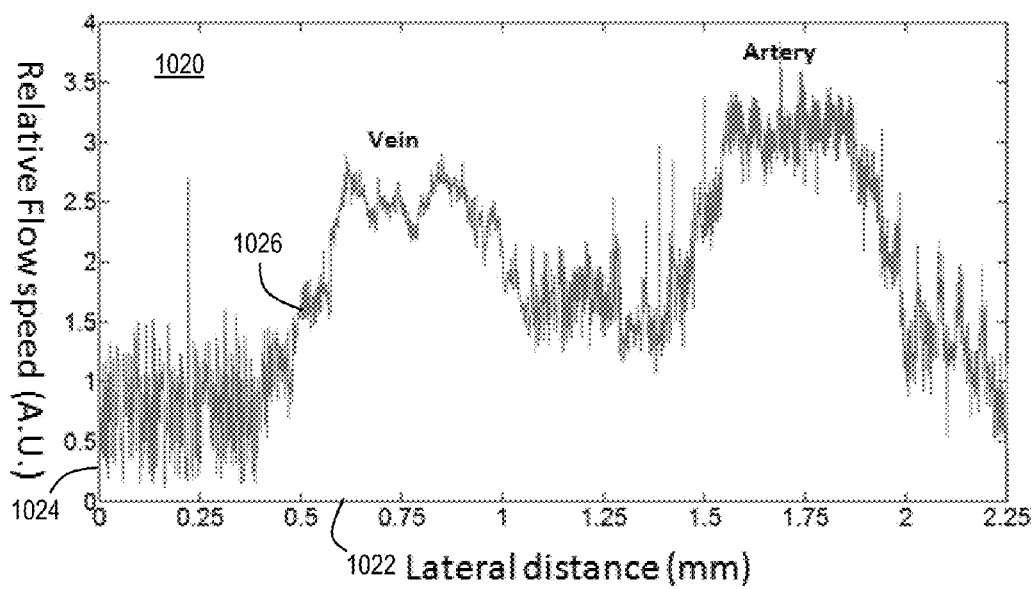
FIG. 10B through FIG. 10C are graphs that illustrate results of the application of FIG. 10A, according to an embodiment.
Figure 10C:
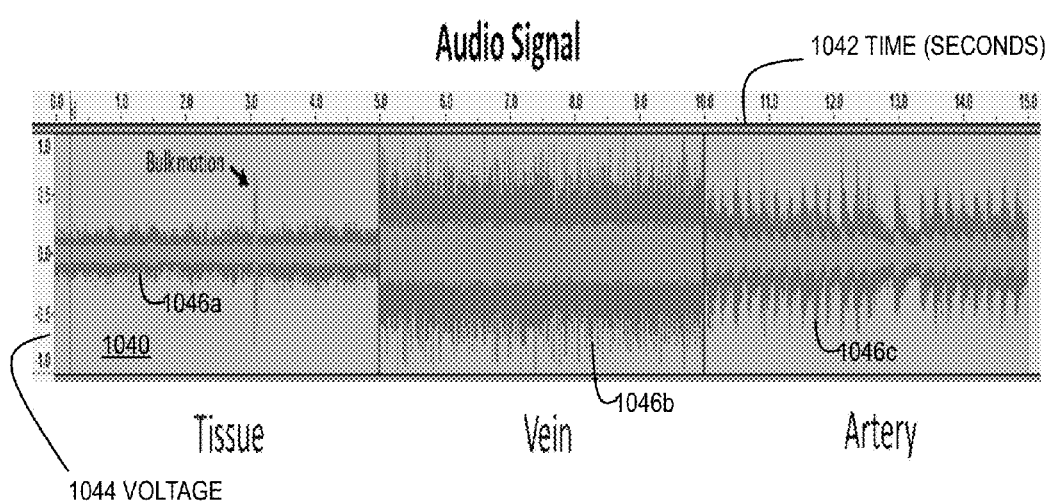

FIG. 10B through FIG. 10C are graphs 1020 and 1040 that illustrate results of the application of FIG. 10A, according to an embodiment. Graph 1020 in FIG. 10B has a horizontal axis 1022 that represents the lateral distance moved in millimeters. The vertical axis 1024 indicates the relative flow speed in arbitrary units. Trace 1026 shows the relative flow speed as a function of distance moved by the probe tip. The flow speed is acquired by placing the probe at different location (0.1 mm interval) for ten seconds. The vessels that are separated by only 1 mm apart were clearly differentiated. FIG. 10B demonstrates that the probe has good lateral resolution to differentiate the vessels that are only separated by 1 mm.

Graph 1040 in FIG. 10C has a horizontal axis 1042 that represents the time in seconds while the probe is moved over the tissue. The vertical axis 1044 indicates the audio signal voltage. Trace 1046a, 1046b and 1046c shows the audio signal driving amplitude as a function of time and shows that the audio signal of tissue, vein and artery are very different. The venous audio signal 1046b is louder than the tissue signal 1046a and the arterial audio signal 1046c has very clear pulsation pattern. Also the bulk motion of the probe relative to the sample has very high pitch tones that can be easily differentiated from the vessel signals. This data demonstrates the CGD probe's ability to resolve vessels that are very close to each other. The audio signal can indicate both the vessel type and flow speed.

Ex Vivo Human Tooth Crown Root Junction.

Figure 11A:
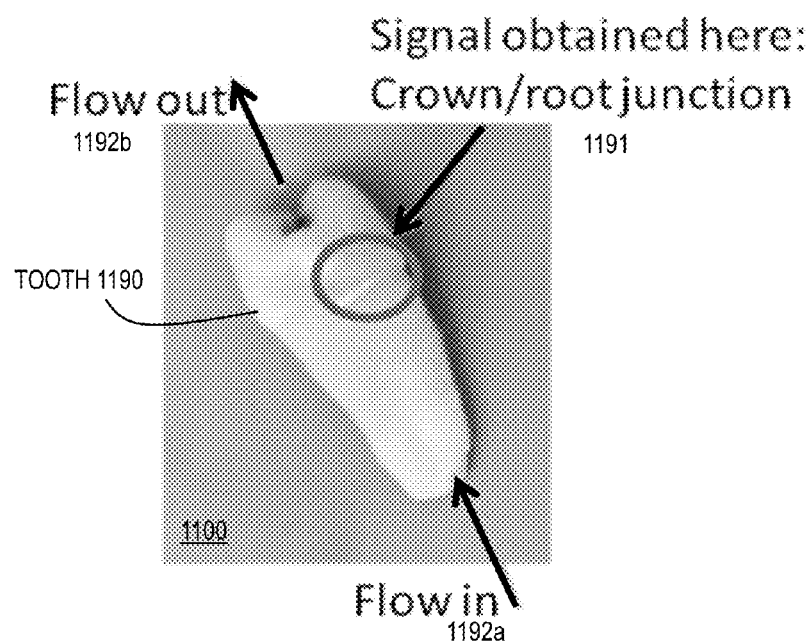
FIG. 11A is an image that illustrates an example application of a CGD apparatus, according to another embodiment.

A different system configuration depicted in FIG. 7 was tested to improve the sensitivity of flow detection in ex vivo human teeth. A laser diode light source with a wavelength of 1300 nm and a bandwidth of 3 nm was coupled to a single mode fiber (probe 730a) with a core size of 5 μm. FIG. 11A is an image 1100 that illustrates an example application of a CGD apparatus 700 to tooth 1190, according to another embodiment. Fiber (probe 730a) was used to illuminate tooth 1190 at the crown/root junction 1191. A multimode fiber with a core size of 50 μm was used as probe 730b to collect scattered light on the opposite side of the tooth 1190. The light was transmitted through a tooth section of 4 mm.

Figure 11B:
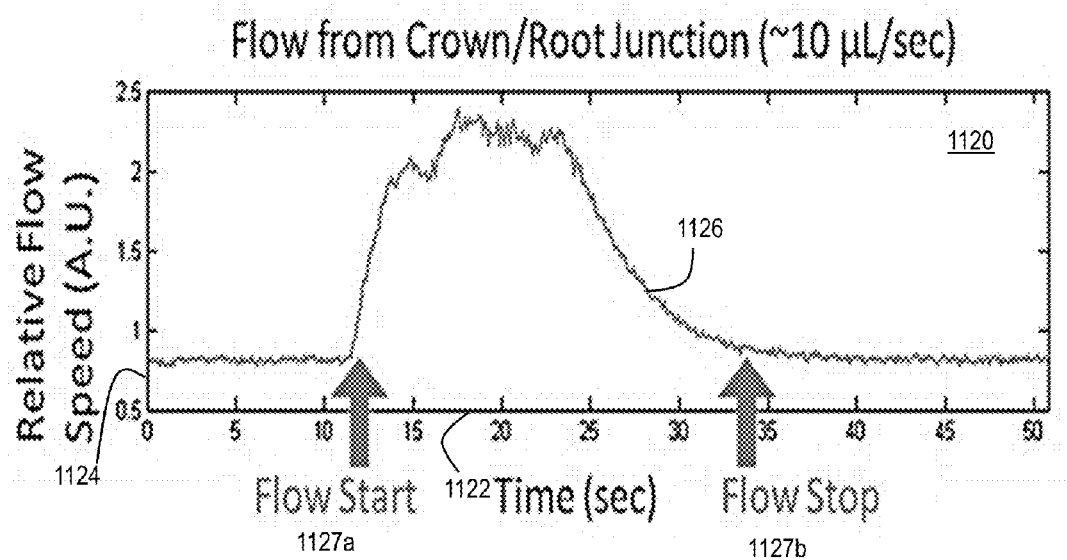
FIG. 11B is a graph that illustrates results of the application of FIG. 11A, according to an embodiment.

A 1% intralipid solution was flowed through the tooth 1190 by entering the root 1192a and exiting at a hole 1192b drilled in the top of the crown. A constant flow speed of 10 microliters per second (μl/s, 1 μl=$10^{-6}$ liters) was used for 12 seconds. FIG. 11B is a graph 1120 that illustrates results of the application of FIG. 11A, according to an embodiment. Graph 1120 has horizontal axis 1122 that indicates time of measurement in seconds. Vertical axis 1124 indicates relative speed in arbitrary units. Trace 1126 shows the relative speed as a function of time of measurement. A constant flow speed is observed in trace 1126 for 12 seconds from 12 to 24 seconds from time zero, with a dwindling flow thereafter for another 10 seconds to about 34 seconds from time zero. Thus, once the applied pressure ceased, the decay in flow speed was observed. A signal-to-noise ratio of 89 was observed.

In Vivo Deep Sheep Brain Vessel Detection

The GCD of FIG. 3B was used in this application, including dual balanced detection circuit 380. The light source 350 was a laser diode at 1310 nm (Qphotonics QFLD-1300-10S of Ann Arbor, Mich.). The wavelength bandwidth of the light source was 3 nm, and thus the coherence length was 190 μm in water. The fiber coupler 363a split the photons 90% to emitted light path and 10% to reference path. The optical fiber circulator 361 sent the illumination light from port 1 to port 2 and the backscattered light from port 2 to port 3. Both back scattered light from the sample and the reference light from the reference mirror went to another fiber coupler 362 where interference occurs. The fiber coupler 362 split the interfering photons evenly (50% and 50%, respectively) between two output fibers that impinged different detectors of the dual balanced detection circuit 380, which rejected the common mode noise and output an electronic signal. After further amplification and frequency filtering (e.g., band pass from 10 Hz to ~20,000 Hz), the processed electronic signal was converted to an analog audio signal and presented by a speaker 385 without an intervening ADC. The signal was also collected by a data acquisition (DAQ) card (National Instrument NI-6259 of Austin Tex.) serving as ADC 386 and processed with the computer system 388. The sampling rate of data acquisition was 400 kHz. The fiber probe 371 consisted of a single mode fiber (SM) and a GRIN multimode fiber (GM) for focusing (St. Jude Medical of St. Paul, Minn.). The focal distance was 1.5 mm and the lateral resolution was 40 μm.

Figure 12:
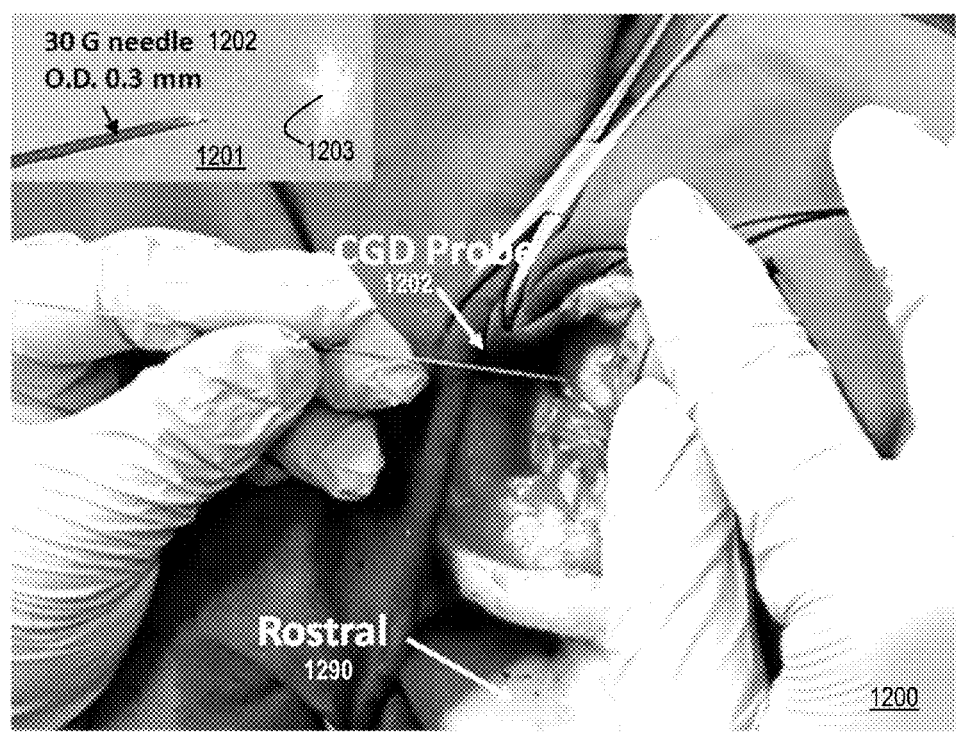
FIG. 12 is an image that illustrates an example application of a CGD apparatus, according to another embodiment.

FIG. 12 is an image 1200 that illustrates an example application of a CGD apparatus 350, according to another embodiment. The performance of the CGD hand-held needle probe 1202 based on the device 350 from FIG. 3B was tested for detecting vessels deep in the sheep brain. Inset 1201 depicts a close-up of the needle 1202 tip serving as probe tip 373 and the light 1203 emitted from the tip.

FIG. 13A through FIG. 13C are graphs that illustrate results of the application of FIG. 12, according to an embodiment. The graphs indicate the voltage waveform, the autocorrelation, and the spectrogram from tissue (FIG. 13A graphs 1310a, 1320a and 1330a, respectively); vein (FIG. 13B graphs 1310b, 1320b and 1330b, respectively), and artery (FIG. 13C graphs 1310c, 1320c and 1330c, respectively). The horizontal axis 1302 indicates measurement time in seconds, and is the same for all nine graphs. The vertical axis 1314 indicates audio signal waveform in volts and is the same for graphs 1310a, 1310b and 1310c. The vertical axis 1324 indicates autocorrelation in arbitrary units and is the same for graphs 1320a, 1320b and 1320c. The vertical axis 1334 indicates audio signal frequency in kiloHertz and is the same for graphs 1330a, 1330b and 1330c.

When the CGD probe is surrounded by highly scattering brain tissues depicted in FIG. 13A, any relative motion between the probe and the brain generates very strong Doppler signal. The spectrogram 1330 shows that the signal is strong (large volume of scatters) with focused frequency range (uniform speed). In contrast, the signal from a vein depicted in graph 1330b is more homogeneous in the frequency domain. The waveform 1310c of an artery shows the pulsation pattern, and the spectrogram 1330c reveals the speed variation during a pulsation cycle. When the bulk motion (tissue movement with respect to the CGD probe during insertion) signal is mixed with the artery signal, it may be challenging to differentiate them in the spectrogram. However, if one studies the similarity of the time domain signal by autocorrelation in graphs 1320a, 1320b and 1320c, a clear difference can be seen between the bulk motion 1320a and the artery 1320c. The difference of the frequency distribution between different spikes in the bulk motion spectrogram is found to generate irregular fluctuation on Acorr 1320a, which is distinctively different from the periodic Acorr of the artery 1320c. In FIG. 13A, from 4.5 seconds to 5 seconds, the probe is static and the bulk motion is significantly lower than the signal in other time periods. Acorr of the vein 1320b remains in a constant level due to the homogeneity of the signal. This data demonstrates that the CGD probe can differentiate and detect blood vessels in the solid tissue without imaging guidance.

Ultrasound-Guided CGD Vessel Detection

Figure 14A:
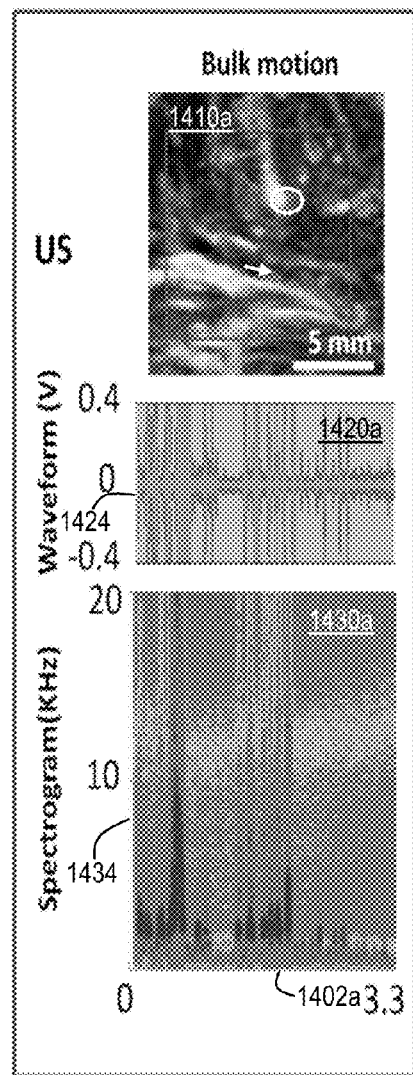
FIG. 14A through FIG. 14C are graphs that illustrate results of another application of a CGD apparatus, according to an embodiment.
Figure 14B:
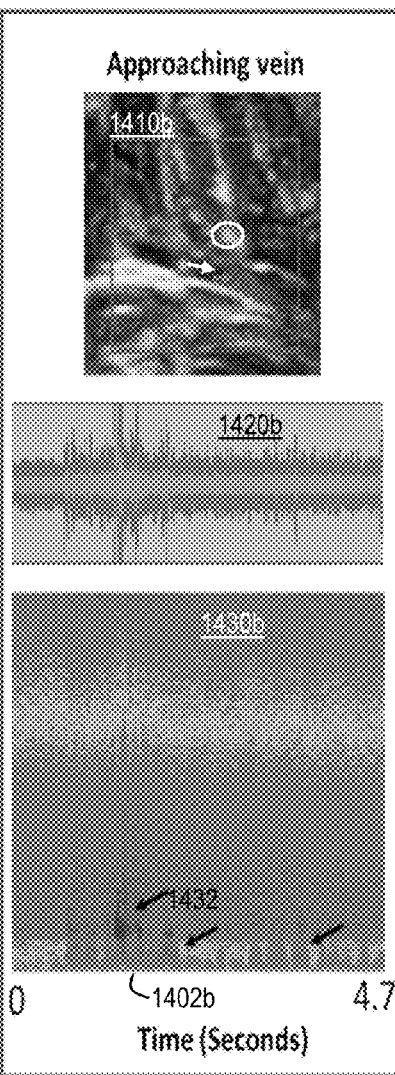
Figure 14C:
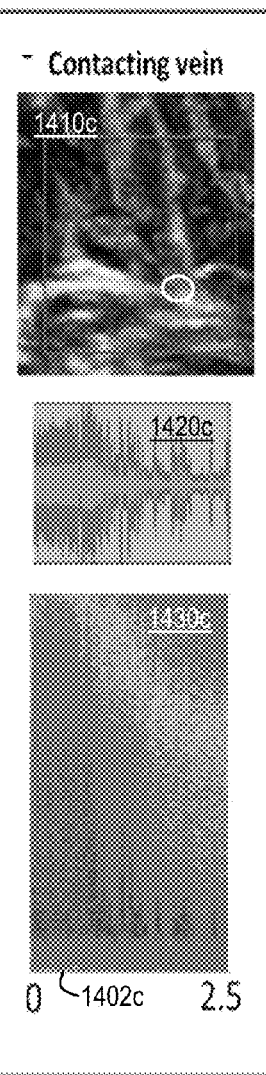

FIG. 14A through FIG. 14C are graphs that illustrate results of another application, according to an embodiment. The graphs indicate ultrasound image, voltage waveform, and the spectrogram from tissue (FIG. 14A graphs 1410a, 1420a and 1430a, respectively); vein (FIG. 14B graphs 1410b, 1420b and 1430b, respectively), and artery (FIG. 14C graphs 1410c, 1420c and 1430c, respectively). The horizontal axes 1402a, 1402b and 1402c, respectively indicate measurement time in seconds. The vertical axis 1424 indicates audio signal waveform in volts and is the same for graphs 1420a, 1420b and 1420c. The vertical axis 1434 indicates audio signal frequency in kiloHertz and is the same for graphs 1430a, 1430b and 1430c The CGD probe embodiment used in this application is described in FIG. 3B. To verify that the CGD probe can detect blood vessels in highly scattering tissues, a CGD probe was pushed toward a blood vessel in the sheep brain under ultrasound (US) guidance. FIG. 14A shows the situation when the probe (indicated by circle in image 1410a) is 1-4 mm away from the vessel (indicated by arrow). The signal is dominated by bulk motion. The blood flow signal was initially detected at distance 3 mm in front of the needle. Similar to the signal from the femoral vessel data (FIG. 13A), the bulk motion has high intensity and focused frequency distribution in graph 1430a. As the probe approaches the vessel (<1 mm), the blood flow signal shows a uniform frequency distribution (graph 1430b in FIG. 14B). FIG. 14B also shows that the blood flow signal was mixed with bulk motion signal (indicated by black arrows 1432). Lastly, when the CGD probe comes in contact with the vessel in image 1410c, the blood flow signal graph 1420c initially becomes stronger followed by a loss of the CGD flow signal. The probe is advanced until it constricts the flow and the ultrasound signal is lost; the CGD signal also attenuates. This data demonstrates that the CGD probe can detect blood vessels in the solid tissue with imaging guidance.

4. COMPUTATIONAL HARDWARE OVERVIEW

Figure 15:
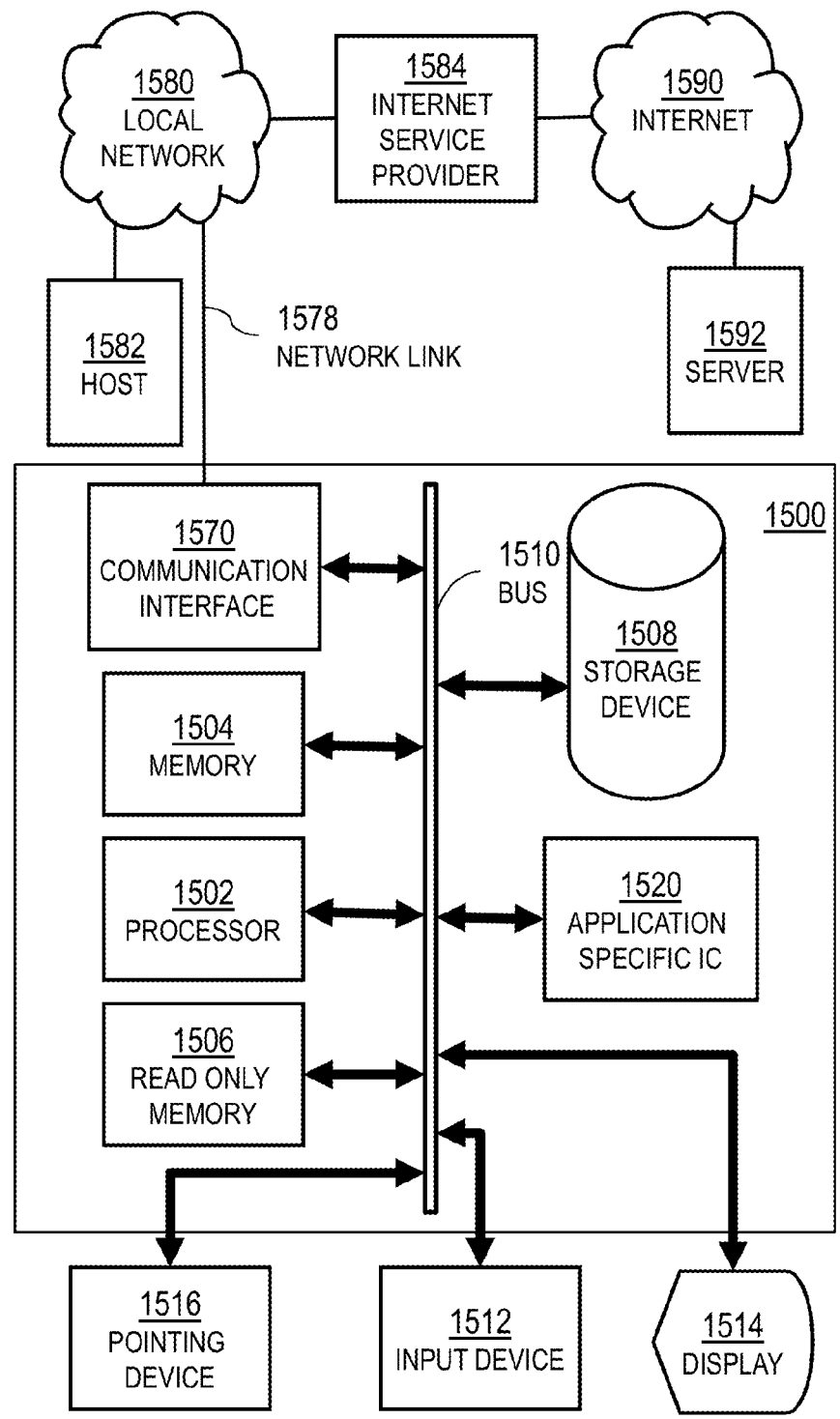
FIG. 15 is a block diagram that illustrates a computer system upon which a portion of an embodiment of the invention may be implemented.
Figure 16:
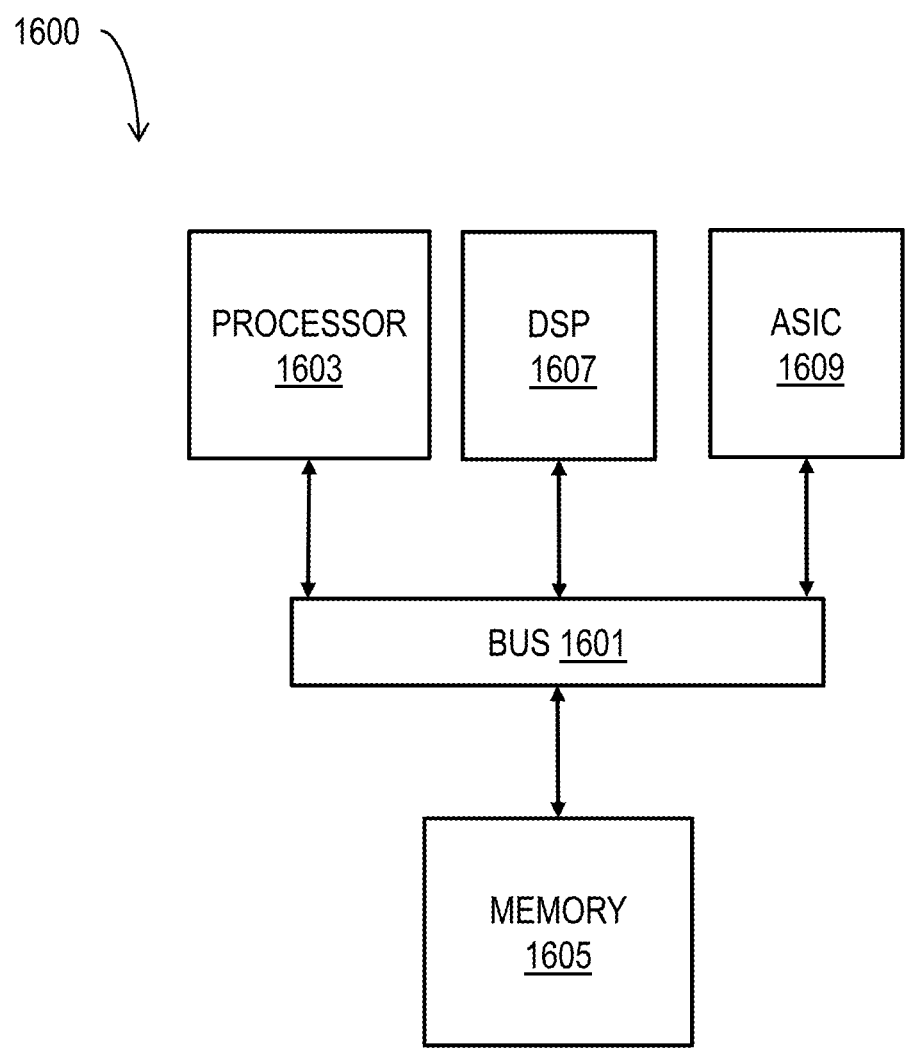
FIG. 16 illustrates a chip set 1600 upon which a portion of an embodiment of the invention may be implemented.

FIG. 15 is a block diagram that illustrates a computer system 1500 upon which a portion of an embodiment of the invention may be implemented. Computer system 1500 includes a communication mechanism such as a bus 1510 for passing information between other internal and external components of the computer system 1500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1500, or a portion thereof, constitutes a means for performing one or more steps of one or more methods described herein.

A sequence of binary digits constitutes digital data that is used to represent a number or code for a character. A bus 1510 includes many parallel conductors of information so that information is transferred quickly among devices coupled to the bus 1510. One or more processors 1502 for processing information are coupled with the bus 1510. A processor 1502 performs a set of operations on information. The set of operations include bringing information in from the bus 1510 and placing information on the bus 1510. The set of operations also typically include comparing two or more units of information, shifting positions of units of information, and combining two or more units of information, such as by addition or multiplication. A sequence of operations to be executed by the processor 1502 constitutes computer instructions.

Computer system 1500 also includes a memory 1504 coupled to bus 1510. The memory 1504, such as a random access memory (RAM) or other dynamic storage device, stores information including computer instructions. Dynamic memory allows information stored therein to be changed by the computer system 1500. RAM allows a unit of information stored at a location called a memory address to be stored and retrieved independently of information at neighboring addresses. The memory 1504 is also used by the processor 1502 to store temporary values during execution of computer instructions. The computer system 1500 also includes a read only memory (ROM) 1506 or other static storage device coupled to the bus 1510 for storing static information, including instructions, that is not changed by the computer system 1500. Also coupled to bus 1510 is a non-volatile (persistent) storage device 1508, such as a magnetic disk or optical disk, for storing information, including instructions, that persists even when the computer system 1500 is turned off or otherwise loses power.

Information, including instructions, is provided to the bus 1510 for use by the processor from an external input device 1512, such as a keyboard containing alphanumeric keys operated by a human user, or a sensor. A sensor detects conditions in its vicinity and transforms those detections into signals compatible with the signals used to represent information in computer system 1500. Other external devices coupled to bus 1510, used primarily for interacting with humans, include a display device 1514, such as a cathode ray tube (CRT) or a liquid crystal display (LCD), for presenting images, and a pointing device 1516, such as a mouse or a trackball or cursor direction keys, for controlling a position of a small cursor image presented on the display 1514 and issuing commands associated with graphical elements presented on the display 1514.

In the illustrated embodiment, special purpose hardware, such as an application specific integrated circuit (IC) 1520, is coupled to bus 1510. The special purpose hardware is configured to perform operations not performed by processor 1502 quickly enough for special purposes. Examples of application specific ICs include graphics accelerator cards for generating images for display 1514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1500 also includes one or more instances of a communications interface 1570 coupled to bus 1510. Communication interface 1570 provides a two-way communication coupling to a variety of external devices that operate with their own processors, such as printers, scanners and external disks. In general the coupling is with a network link 1578 that is connected to a local network 1580 to which a variety of external devices with their own processors are connected. For example, communication interface 1570 may be a parallel port or a serial port or a universal serial bus (USB) port on a personal computer. In some embodiments, communications interface 1570 is an integrated services digital network (ISDN) card or a digital subscriber line (DSL) card or a telephone modem that provides an information communication connection to a corresponding type of telephone line. In some embodiments, a communication interface 1570 is a cable modem that converts signals on bus 1510 into signals for a communication connection over a coaxial cable or into optical signals for a communication connection over a fiber optic cable. As another example, communications interface 1570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1570 sends and receives electrical, acoustic or electromagnetic signals, including infrared and optical signals, that carry information streams, such as digital data.

The term computer-readable medium is used herein to refer to any medium that participates in providing information to processor 1502, including instructions for execution.

Such a medium may take many forms, including, but not limited to, non-volatile media, volatile media and transmission media. Non-volatile media include, for example, optical or magnetic disks, such as storage device 1508. Volatile media include, for example, dynamic memory 1504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1502, except for carrier waves and other signals.

Logic encoded in one or more tangible media includes one or both of processor instructions on a computer-readable storage media and special purpose hardware, such as ASIC 1520.

Network link 1578 typically provides information communication through one or more networks to other devices that use or process the information. For example, network link 1578 may provide a connection through local network 1580 to a host computer 1582 or to equipment 1584 operated by an Internet Service Provider (ISP). ISP equipment 1584 in turn provides data communication services through the public, world-wide packet-switching communication network of networks now commonly referred to as the Internet 1590. A computer called a server 1592 connected to the Internet provides a service in response to information received over the Internet. For example, server 1592 provides information representing video data for presentation at display 1514.

The invention is related to the use of computer system 1500 for implementing the techniques described herein. According to one embodiment of the invention, those techniques are performed by computer system 1500 in response to processor 1502 executing one or more sequences of one or more instructions contained in memory 1504. Such instructions, also called software and program code, may be read into memory 1504 from another computer-readable medium such as storage device 1508. Execution of the sequences of instructions contained in memory 1504 causes processor 1502 to perform the method steps described herein. In alternative embodiments, hardware, such as application specific integrated circuit 1520, may be used in place of or in combination with software to implement the invention. Thus, embodiments of the invention are not limited to any specific combination of hardware and software.

The signals transmitted over network link 1578 and other networks through communications interface 1570, carry information to and from computer system 1500. Computer system 1500 can send and receive information, including program code, through the networks 1580, 1590 among others, through network link 1578 and communications interface 1570. In an example using the Internet 1590, a server 1592 transmits program code for a particular application, requested by a message sent from computer 1500, through Internet 1590, ISP equipment 1584, local network 1580 and communications interface 1570. The received code may be executed by processor 1502 as it is received, or may be stored in storage device 1508 or other non-volatile storage for later execution, or both. In this manner, computer system 1500 may obtain application program code in the form of a signal on a carrier wave.

Various forms of computer readable media may be involved in carrying one or more sequence of instructions or data or both to processor 1502 for execution. For example, instructions and data may initially be carried on a magnetic disk of a remote computer such as host 1582. The remote computer loads the instructions and data into its dynamic memory and sends the instructions and data over a telephone line using a modem. A modem local to the computer system 1500 receives the instructions and data on a telephone line and uses an infra-red transmitter to convert the instructions and data to a signal on an infra-red a carrier wave serving as the network link 1578. An infrared detector serving as communications interface 1570 receives the instructions and data carried in the infrared signal and places information representing the instructions and data onto bus 1510. Bus 1510 carries the information to memory 1504 from which processor 1502 retrieves and executes the instructions using some of the data sent with the instructions. The instructions and data received in memory 1504 may optionally be stored on storage device 1508, either before or after execution by the processor 1502.

FIG. 16 illustrates a chip set 1600 upon which a portion of an embodiment of the invention may be implemented. Chip set 1600 is programmed to perform one or more steps of a method described herein and includes, for instance, the processor and memory components described with respect to FIG. 15 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1600, or a portion thereof, constitutes a means for performing one or more steps of a method described herein.

In one embodiment, the chip set 1600 includes a communication mechanism such as a bus 1601 for passing information among the components of the chip set 1600. A processor 1603 has connectivity to the bus 1601 to execute instructions and process information stored in, for example, a memory 1605. The processor 1603 may include one or more processing cores with each core configured to perform independently. A multi-core processor enables multiprocessing within a single physical package. Examples of a multi-core processor include two, four, eight, or greater numbers of processing cores. Alternatively or in addition, the processor 1603 may include one or more microprocessors configured in tandem via the bus 1601 to enable independent execution of instructions, pipelining, and multithreading. The processor 1603 may also be accompanied with one or more specialized components to perform certain processing functions and tasks such as one or more digital signal processors (DSP) 1607, or one or more application-specific integrated circuits (ASIC) 1609. A DSP 1607 typically is configured to process real-world signals (e.g., sound) in real time independently of the processor 1603. Similarly, an ASIC 1609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1603 and accompanying components have connectivity to the memory 1605 via the bus 1601. The memory 1605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1605 also stores the data associated with or generated by the execution of one or more steps of the methods described herein.

5. EXTENSIONS, MODIFICATIONS AND ALTERNATIVES

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

6. REFERENCES

A. Ahmad, S G. Adie, M Wang, and S A. Boppart, "Sonification of optical coherence tomography data and images," *Opt. Express* v18, pp 9934-9944 (2010).

C. Andrews, I. Aviles-Olmos, M. Hariz, and T. Foltynie, "Which patients with dystonia benefit from deep brain stimulation? A metaregression of individual patient outcomes," *Journal of Neurology Neurosurgery and Psychiatry* v81, pp 1383-1389 (2010).

D. K. Binder, G. M. Rau, and P. A. Starr, "Hemorrhagic complications of microelectrode-guided deep brain stimulation," *Stereotactic and Functional Neurosurgery* v80, pp 28-31 (2003).

D. K. Binder, G. M. Rau, and P. A. Starr, "Risk factors for hemorrhage during microelectrode-guided deep brain stimulator implantation for movement disorders," *Neurosurgery* v56, pp 22-732; discussion pp 722-732 (2005).

J. M. Bronstein, M. Tagliati, R. L. Alternan, A. M. Lozano, J. Volkmann, A. Stefani, F. B. Horak, M. S. Okun, K. D. Foote, P. Krack, R. Pahwa, J. M. Henderson, M. I. Hariz, R. A. Bakay, A. Rezai, W. J. Marks, Jr., E. Moro, J. L. Vitek, F. M. Weaver, R. E. Gross, and M. R. DeLong, "Deep brain stimulation for Parkinson disease: an expert consensus and review of key issues," *Archives of Neurology* v68, p 165 (2010).

D. J. Caplan, J. B. Chasen, E. A. Krall, J. Cai, S. Kang, R. I. Garcia, S. Offenbacher, J. D. Beck, "Lesions of endodontic origin and risk of coronary heart disease," *Journal of Dental Research* v85 n11, pp 996-1000 (2006).

Z. P. Chen, T. E. Milner, S. Srinivas, X. J. Wang, A. Malekafzali, M. J. C. vanGemert, and J. S. Nelson, "Noninvasive imaging of in vivo blood flow velocity using optical Doppler tomography," *Optics Letters* v22, pp 1119-1121 (1997).

G. Deuschl, J. Herzog, G. Kleiner-Fisman, C. Kubu, A. M. Lozano, K. E. Lyons, M. C. Rodriguez-Oroz, F. Tamma, A. I. Troster, J. L. Vitek, J. Volkmann, and V. Voon, "Deep brain stimulation: Postoperative issues," *Movement Disorders* v21, pp S219-S237 (2006).

H. C. Eun, "Evaluation of skin blood flow by laser Doppler flowmetry," *Clin Dermatol* v13, pp 337-347 (1995).

E. D. Flora, C. L. Perera, A. L. Cameron, and G. J. Maddern, "Deep Brain Stimulation for Essential Tremor: A Systematic Review," *Movement Disorders* v25, pp 1550-1559 (2010).

I. Fredriksson, C. Fors, and J. Johansson, "Laser Doppler Flowmetry—A Theoretical Framework," Department of Biomedical Engineering, Linköping University (2007).

B. Gazelius, L. Olgart, and B. Edwall, "Restored vitality in luxated teeth assessed by laser Doppler flowmeter," *Endodontics & Dental Traumatology* v4, pp 265-268 (1988).

A. Gorgulho, A. A. De Salles, L. Frighetto, and E. Behnke, "Incidence of hemorrhage associated with electrophysiological studies performed using macroelectrodes and microelectrodes in functional neurosurgery," *Journal of Neurosurgery* v102, pp 888-896 (2005).

M. I. Hariz, "Complications of deep brain stimulation surgery," *Movement Disorders* v17, pp S162-S166 (2002).

R. S. Jones, G. D. Huynh, G. C. Jones, and D. Fried, "Near-infrared transillumination at 1310-nm for the imaging of early dental decay," *Optics Express* v11, pp 2259-2265 (2003).

K. Kijsamanmith, S. Timpawat, N. Vongsavan, and B. Matthews, "Pulpal blood flow recorded from human premolar teeth with a laser Doppler flow meter using either red or infrared light," *Arch Oral Biol* v56, pp 629-633 (2011).

P. N. Kongkham, E. Knifed, M. S. Tamber, and M. Bernstein, "Complications in 622 cases of frame-based stereotactic biopsy, a decreasing procedure," *Canadian Journal of Neurological Sciences* v35, pp 79-84 (2008).

A. V. Kulkarni, A. Guha, A. Lozano, and M. Bernstein, "Incidence of silent hemorrhage and delayed deterioration after stereotactic brain biopsy," *Journal of Neurosurgery* v89, pp 31-35 (1998).

P. Mohr, "Deep Brain Stimulation in Psychiatry," Neuroendocrinology Letters v29, pp 123-132 (2008). M. Nishihara, T. Sasayama, H. Kudo, and E. Kohmura, "Morbidity of stereotactic biopsy for intracranial lesions," *Kobe Journal of Medical Sciences* v56, pp E148-153 (2010).

W. C. Noblett, L. R. Wilcox, F. Scamman, W. T. Johnson, and A. Diaz-Arnold, "Detection of pulpal circulation in vitro by pulse oximetry," *Journal of Endodontics* v22, pp 1-5 (1996).

L. Olgart, B. Gazelius, and U. Lindh-Stromberg, "Laser Doppler flowmetry in assessing vitality in luxated permanent teeth," *International Endodontic Journal* v21, pp 300-306 (1988).

K. Petersson, C. Soderstrom, M. Kiani-Anaraki, and G. Levy, "Evaluation of the ability of thermal and electrical tests to register pulp vitality," *Endodontics & Dental Traumatology* v15, pp 127-131 (1999).

G. Podoleanu, "Unbalanced versus balanced operation in an optical coherence tomography system," *Applied Optics* v39, pp 173-182 (2000).

M. H. Pozzobon, R. de Sousa Vieira, A. M. Alves, J. Reyes-Carmona, C. S. Teixeira, B. D. de Souza, and W. T. Felippe, "Assessment of pulp blood flow in primary and permanent teeth using pulse oximetry," *Dental Traumatology* v27, pp 184-188 (2011).

C. A. Sansur, R. C. Frysinger, N. Pouratian, K. M. Fu, M. Bittl, R. J. Oskouian, E. R. Laws, and W. J. Elias, "Incidence of symptomatic hemorrhage after stereotactic electrode placement," *Journal of Neurosurgery* v107, pp 998-1003 (2007).

J. M. Schmitt, R. L. Webber, and E. C. Walker, "Optical determination of dental pulp vitality," *IEEE Transactions on Biomedical Engineering* v38, pp 346-352 (1991).

F. M. Skidmore, R. L. Rodriguez, H. H. Fernandez, W. K. Goodman, K. D. Foote, and M. S. Okun, "Lessons learned in deep brain stimulation for movement and neuropsychiatric disorders," *CNS Spectrums* v11, pp 521+ (2006).

S. Soo-ampon, N. Vongsavan, M. Soo-ampon, S. Chuckpaiwong, and B. Matthews, "The sources of laser Doppler blood-flow signals recorded from human teeth," *Archives of Oral Biology* v48, pp 353-360 (2003).

T. Terao, H. Takahashi, F. Yokochi, M. Taniguchi, R. Okiyama, and I. Hamada, "Hemorrhagic complication of stereotactic surgery in patients with movement disorders," *Journal of Neurosurgery* v98, pp 1241-1246 (2003).

B. Varghese, V. Rajan, T. G. Van Leeuwen, and W. Steenbergen, "Path-length-resolved measurements of multiple scattered photons in static and dynamic turbid media using phase modulated low-coherence interferometry," *Journal of Biomedical Optics* v12 (2007).

J. Voges, R. Hilker, K. Botzel, K. L. Kiening, L. Moss, A. Kupsch, A. Schnitzler, G. H. Schneider, U. Steude, G. Deuschl, and M. O. Pinsker, "Thirty days complication rate following surgery performed for deep-brain-stimulation," *Movement Disorders* v22, pp 1486-1489 (2007).

K. Wardell, P. Blomstedt, J. Richter, J. Antonsson, O. Eriksson, P. Zsigmond, A. T. Bergenheim, and M. I. Hariz, "Intracerebral microvascular measurements during deep brain stimulation implantation using laser Doppler perfusion monitoring," *Stereotactic and Functional Neurosurgery* v85, pp 279-286 (2007).

R. Weisleder, S. Yamauchi, D. J. Caplan, M. Trope, and F. B. Teixeira, "The validity of pulp testing: a clinical study," *Journal of the American Dental Association* v140, pp 1013-1017 (2009).

V. X. D. Yang, M. L. Gordon, B. Qi, J. Pekar, S. Lo, E. Seng-Yue, A. Mok, B. C. Wilson, and I. A. Vitkin, "High speed, wide velocity dynamic range Doppler optical coherence tomography (Part I): System design, signal processing, and performance," *Opt Express* v11, pp 794-809 (2003).

What is claimed is:

1. An apparatus comprising:
    an optical source of light comprising a band of wavelengths with a bandwidth that is in a range between 0.1% and 2.9% of a center wavelength of the band of wavelengths;
    an optical detector;
    a first optical coupler configured to direct light from the optical source through an emission optical path that terminates at a distal end in a single probe tip;
    a second optical coupler configured to direct onto the optical detector scattered light returning from the single probe tip through a return optical path; and
    a presentation device configured to output a signal that indicates motion in a target volume of a sample in a vicinity of the single probe tip based on a Doppler shift between the light from the light source and the scattered light received at the detector through the single probe tip,
    whereby the target volume is based on a coherence distance determined by the bandwidth of the band of wavelengths of the light from the optical source.

2. An apparatus as recited in claim 1, wherein the first optical coupler and second optical coupler includes a single optical fiber connected to the single probe tip, and the single optical fiber is multimode fiber.

3. An apparatus as recited in claim 1, wherein the single probe tip is configured to be hand held.

4. An apparatus as recited in claim 1, wherein the bandwidth is in a range between 0.2% and 2.9% of a center wavelength of the band of wavelengths.

5. An apparatus as recited in claim 1, wherein the bandwidth is about 3 nanometers and a center wavelength is about 1300 nanometers whereby axial spatial resolution of about 1 millimeter is provided.

6. An apparatus as recited in claim 1, wherein:
    the optical detector comprises a dual balanced detection circuit that comprises two detectors; and,
    the second optical coupler is configured to direct onto each detector in the dual balanced detection circuit an approximately equal portion of the scattered light returning from the single probe tip through the return optical path.

7. An apparatus as recited in claim 1, further comprising a third optical coupler configured to direct light from the optical source through a reference optical path onto the optical detector to produce an interference beat frequency with the scattered light at the detector.

8. An apparatus as recited in claim 7, wherein the presentation device is an acoustic speaker configured to output an acoustic frequency based on the interference beat frequency at the detector.

9. An apparatus as recited in claim 8, wherein the acoustic speaker is an analog acoustic speaker and the detector outputs an analog electronic signal and the speaker is driven by the analog electronic signal from the detector without an intervening analog to digital converter.

10. An apparatus as recited in claim 7, wherein a depth in the sample of the target volume is based on a coherence of the scattered light with the light from the optical source through the reference optical path.

11. An apparatus as recited in claim 10, the reference optical path further comprising an optical component configured to adjustably set a length of the reference optical path.

12. An apparatus as recited in claim 10, the reference optical path further comprising an optical component configured to fix a length of the reference optical path.

13. An apparatus comprising:
    an optical source of light comprising a band of wavelengths with a bandwidth that is in a range between 0.1% and 2.9% of a center wavelength of the band of wavelengths;
    an optical detector;
    a first optical coupler configured to direct light from the optical source through an emission optical path that terminates at a distal end in a first probe tip;
    a second optical coupler configured to direct, onto the optical detector, through a return optical path that terminates at a distal end in a second probe tip, light that enters the second probe tip from outside the second probe tip; and a presentation device configured to output a signal that indicates motion in a target volume of a sample in a vicinity of the first probe tip and second probe tip based on a Doppler shift between the light from the light source emitted through the first probe tip and the scattered light received at the detector through the second probe tip, whereby the target volume is based on a coherence distance determined by the bandwidth of the band of wavelengths of the light from the optical source.

14. An apparatus as recited in claim 13, wherein the second probe tip and the first probe tip are configured to be hand held.

15. An apparatus as recited in claim 13, wherein the second probe tip is different from the first probe tip.

16. An apparatus as recited in claim 15, wherein the first probe tip and the second probe tip are configured for collecting transmitted light through the sample.

17. An apparatus as recited in claim 13, wherein the bandwidth is in a range between 0.2% and 2.9% of a center wavelength of the band of wavelengths.

18. An apparatus comprising:
an optical source of light comprising a band of wavelengths with a bandwidth that is in a range between 0.1% and 2.9% of a center wavelength of the band of wavelengths;
an optical detector;
a first optical coupler configured to direct light from the optical source through an emission optical path that terminates at a distal end in a first probe tip;
a second optical coupler configured to direct, onto the optical detector, through a return optical path that terminates at a distal end in a second probe tip, light that enters the second probe tip from outside the second probe tip; and
a speaker configured to output a signal that indicates motion in a target volume of a sample in a vicinity of the first probe tip and second probe tip based on interference at the detector,
whereby the target volume is based on a coherence distance determined by a bandwidth of the band of wavelengths of the light from the optical source.

19. An apparatus as recited in claim 18, wherein the second probe tip is the first probe tip.

20. An apparatus as recited in claim 18, wherein the second probe tip is different from the first probe tip.

21. An apparatus as recited in claim 20, wherein the first probe tip and the second probe tip are configured for collecting transmitted light through the sample.

22. An apparatus as recited in claim 18, wherein the first probe tip and the second probe tip are configured to be hand held.

23. An apparatus as recited in claim 18, wherein the bandwidth is in a range between 0.2% and 2.9% of a center wavelength of the band of wavelengths.

24. An apparatus as recited in claim 18, wherein the acoustic speaker is an analog acoustic speaker and the detector outputs an analog electronic signal, and the speaker is driven by the analog electronic signal from the detector without an intervening analog to digital converter.

* * * * *